United States Patent
Messersmith et al.

(10) Patent No.: US 12,269,797 B2
(45) Date of Patent: Apr. 8, 2025

(54) BIFUNCTIONAL LINKER FOR BISCONJUGATION, METHOD OF SYNTHESIS, AND METHOD OF USE

(71) Applicant: The Johns Hopkins University, Baltimore, MD (US)

(72) Inventors: Reid E. Messersmith, Severna Park, MD (US); Scott A. Shuler, Baltimore, MD (US); Mairead E. Bartlett, Takoma Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 862 days.

(21) Appl. No.: 17/488,435

(22) Filed: Sep. 29, 2021

(65) Prior Publication Data

US 2022/0106255 A1  Apr. 7, 2022

Related U.S. Application Data

(60) Provisional application No. 63/088,697, filed on Oct. 7, 2020.

(51) Int. Cl.
| | |
|---|---|
| C07C 69/78 | (2006.01) |
| A61K 47/54 | (2017.01) |
| A61K 49/00 | (2006.01) |
| C07C 51/363 | (2006.01) |
| C07C 67/10 | (2006.01) |
| C07C 67/313 | (2006.01) |
| C07D 209/46 | (2006.01) |
| C08G 61/12 | (2006.01) |

(52) U.S. Cl.
CPC ............ *C07C 69/78* (2013.01); *A61K 47/545* (2017.08); *A61K 49/0045* (2013.01); *A61K 49/0052* (2013.01); *A61K 49/0063* (2013.01); *C07C 51/363* (2013.01); *C07C 67/10* (2013.01); *C07C 67/313* (2013.01); *C07D 209/46* (2013.01); *C08G 61/123* (2013.01); *C07B 2200/09* (2013.01); *C08G 2261/124* (2013.01); *C08G 2261/1422* (2013.01); *C08G 2261/228* (2013.01); *C08G 2261/3221* (2013.01); *C08G 2261/334* (2013.01)

(58) Field of Classification Search
None
See application file for complete search history.

(56) References Cited

PUBLICATIONS

Chun Ling Tung et al., "Traceless and Chemoselective Amine Bioconjugation via Phthalimidine Formation in Native Protein Modification," Org. Lett. 2016, 18, pp. 2600-2603.
Qing Zhang et al. "OPA-Based Bifunctional Linker for Protein Labeling and Profiling," Biochemistry 2020, 59, pp. 175-178.
Yu Zhang et al., "Site-Selective Lysine Reactions Guided by Protein-Peptide Interaction," Biochemistry 2019, 58, pp. 1010-1018.
Yu Zhang et al., "Chemoselective Peptide Cyclization and Bicyclization Directly on Unprotected Peptides," J. Am. Chem. Soc. 2019, 141, pp. 12274-12279.
Unknown, "4-(N-Maleimidomethyl)cyclohexanecarboxylic acid N-hydroxysuccinimide ester," Sigma-Aldrich website (https://www.sigmaaldrich.com/catalog/product/sigma/m5525?lang=en&region=US), last accessed Mar. 8, 2021, pp. 1-4.
Alexander V. Statsuk, et al., "Tuning a Three-Component Reaction for Trapping Kinase Substrate Complexes," J. Am. Chem. Soc., 130, 2008, pp. 17568-17574.

*Primary Examiner* — Michael G. Hartley
*Assistant Examiner* — Samantha L Mejias
(74) *Attorney, Agent, or Firm* — Noah J. Hayward

(57) ABSTRACT

A bifunctional linker of Formula 1

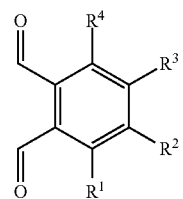

(Formula I)

wherein in Formula I, at least one of $R^1$ to $R^4$ is —$COOR^5$ and $R^5$ is —$C_0$-$C_{10}$alkyl($C_2$-$C_{10}$alkynyl) or —$C_0$-$C_{10}$alkyl-$C_2$-$C_{10}$alkenyl($C_2$-$C_{10}$alkynyl), preferably a terminal alkynyl. The bifunctional linker is used in a cycloaddition to tether two entities, for example a protein or antibody, and an active agent, to form a bisconjugate. The bifunctional linker also be used to form a conjugate, followed by cycloaddition in the presence of a comonomer composition to form a bisconjugate including a protein or antibody linked to an adhesive polymer network. Catalysis can be provided by a copper-containing paint on a surface to adhere the bisconjugate to the surface. Methods of synthesis and use of the bisconjugates imaging, diagnostic, and therapeutic applications are also described.

5 Claims, 12 Drawing Sheets
(6 of 12 Drawing Sheet(s) Filed in Color)

BIFUNCTIONAL LINKER FOR BISCONJUGATION, METHOD OF SYNTHESIS, AND METHOD OF USE

CROSS REFERENCE TO RELATED APPLICATIONS

This application claims priority to and the benefit of prior-filed, U.S. Provisional Application Ser. No. 63/088,697, filed Oct. 7, 2020, the content of which is hereby incorporated by reference in its entirety.

BACKGROUND

This disclosure relates to bifunctional linkers for conjugation of two dissimilar compounds, the bisconjugates formed thereby, methods of their manufacture, and uses thereof, in particular uses to bind the bisconjugates to a variety of substrates.

The ability to harness biology's accuracy and precision in conjunction with synthetic chemistry gives researchers access to a wide range of functionalities that are otherwise difficult to achieve, such as drug-antibody conjugates. Bioconjugation is a powerful tool that allows researchers to make covalent bonds between naturally-occurring molecules and synthetic compounds. Thiols (cysteine) and amines (lysine) are widely used bio-reactive functional groups in such bioconjugation reactions. Thiol conjugation is a well-studied approach due to the high reactivity of thiols with Michael acceptors, but suffers from challenges including the low availability of free cysteines in proteins without mutation or partial denaturation, and linkage instability as a result of thiol exchange or hydrolysis. Amine conjugation forms stable covalent bonds and takes advantage of the natural abundance of lysine amines, and is therefore the basis of most commercially-available bioconjugative linkers. However, amine conjugation, especially those based on N-hydroxylsuccinimide (NHS) esters, are not specific for lysine, and also target other nucleophilic amino acids. There accordingly remains a need in the art for bifunctional coupling agents for amines. It would be particularly useful if the coupling agents were selectively reactive with amines such as lysine in a protein.

SUMMARY

Described herein is a compound of Formula I

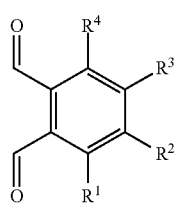
(Formula I)

wherein in Formula I,

R$^1$ to R$^4$ are each independently hydrogen, halogen, cyano, nitro, C$_1$-C$_6$alkyl, C$_0$-C$_6$alkyl(C$_3$-C$_7$cycloalkyl), —C$_0$-C$_6$alkyl(heterocycloalkyl), —C$_0$-C$_6$alkyl(aryl), or —C$_0$-C$_6$alkyl(heteroaryl), wherein groups except hydrogen, halogen, cyano, and nitro are optionally substituted with halogen, cyano, nitro, a C$_1$-C$_6$alkyl, a C$_3$-C$_7$cycloalkyl, a heterocycloalkyl, a heteroaryl, or an aryl, and at least one of R$^1$ to R$^4$ is —COOR$^5$; and R$^5$ is —C$_0$-C$_{10}$alkyl(C$_2$-C$_{10}$alkynyl) or —C$_0$-C$_{10}$alkyl-C$_2$-C$_{10}$alkenyl(C$_2$-C$_{10}$alkynyl).

A method for the synthesis of the compound of Formula I is further described, the method including reacting a dimethylarylcarboxylic acid of Formula 1

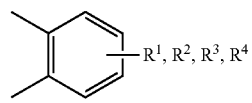
(1)

wherein R$^1$, R$^2$, R$^3$, and R$^4$ are as defined in Formula I except that at least one of R$^1$, R$^2$, R$^3$, and R$^4$ is —COOH, with a halogenating agent to provide a tetrahalomethylarylcarboxylic acid of Formula 2;

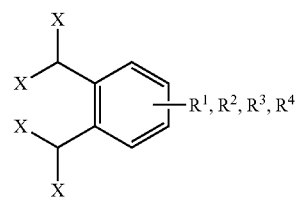
(2)

wherein R$^1$, R$^2$, R$^3$, and R$^4$ are as defined in Formula I, except that at least one of R$^1$, R$^2$, R$^3$, and R$^4$ is —COOH, and X is a halide;

reacting the tetrahalomethylarylcarboxylic acid of Formula 2 with an alkyne compound having a leaving group to afford a carboxylate ester of Formula 3

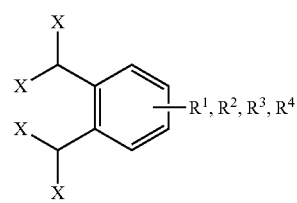
(3)

wherein R$^1$, R$^2$, R$^3$, R$^4$, and R$^5$ are as defined in Formula I, and X is a halide, preferably chlorine or bromine; and oxidizing the carboxylate ester of Formula 3 provide the compound of Formula I.

A conjugate is further described, including a regioisomer of Formula II

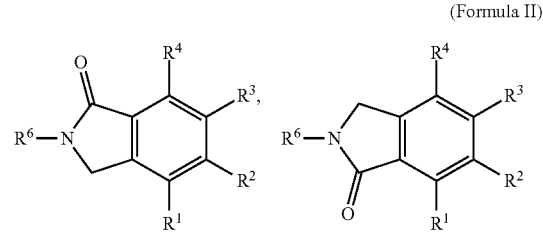
(Formula II)

or a pharmaceutically acceptable salt thereof, wherein in Formula II

R¹ to R⁴ are each independently hydrogen, halogen, cyano, nitro, —$C_1$-$C_{10}$alkyl, —$C_0$-$C_{10}$alkyl($C_2$-$C_{10}$alkynyl), —$C_0$-$C_{10}$alkyl($C_3$-$C_{10}$cycloalkyl), —$C_0$-$C_{10}$alkyl(heterocycloalkyl), —$C_0$-$C_{10}$alkyl(heteroaryl), or —$C_0$-$C_{10}$alkyl(aryl), wherein groups except hydrogen, halogen, cyano, nitro are optionally substituted with halogen, cyano, nitro, a $C_1$-$C_6$alkyl, a $C_3$-$C_7$cycloalkyl, a heterocycloalkyl, a heteroaryl, or an aryl, and at least one of R¹ to R⁴ is —COOR⁵ wherein R⁵ is —$C_1$-$C_{10}$alkyl(alkynyl), or —$C_1$-$C_{10}$alkyl-$C_2$-$C_{10}$alkenyl($C_2$-$C_{10}$alkynyl); and R⁶ is a residue of biomolecule having a primary amine.

A method for the synthesis of the conjugate of Formula II includes reacting a compound of Formula I with a biomolecule including a primary amine.

An article or formulation includes the regioisomer of Formula III or a pharmaceutically acceptable salt thereof. The article or formulation of can be for imaging, treatment of a patient, imaging of a patient, or diagnosis of a patient.

A method of treating a patient in need of treatment with an active agent includes administering to the patient an effective amount of the bisconjugate of Formula III or a pharmaceutically acceptable salt thereof, wherein R⁶ is a residue of a protein or antibody and R⁹ is a residue of an active agent effective for the treatment.

A method of imaging or diagnosing a patient includes administering to the patient in need of imaging or diagnosing an effective amount of the bisconjugate of Formula III or a pharmaceutically effective salt thereof wherein R⁶ is a protein or antibody, and R⁹ is a residue of a biomarker or imaging agent.

Still further described is a bisconjugate of Formula III

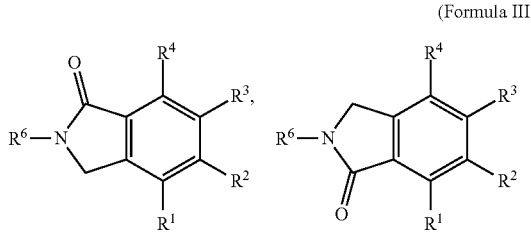

(Formula III)

or a pharmaceutically acceptable salt thereof, wherein in Formula III,

R¹ to R⁴ are each independently hydrogen, halogen, cyano, nitro, —$C_1$-$C_6$alkyl, —$C_0$-$C_6$alkyl($C_3$-$C_7$cycloalkyl), —$C_0$-$C_6$alkyl(heterocycloalkyl), $C_0$-$C_6$alkyl(aryl), or —$C_0$-$C_6$alkyl(heteroaryl), wherein groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl;

at least one of R¹ to R⁴ is —COOR⁷; and

R⁷ is —$C_0$-$C_{10}$alkyl moiety containing a

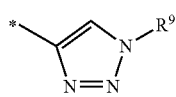

group), or —$C_0$-$C_{10}$alkyl-$C_2$-$C_{10}$alkenyl moiety containing a

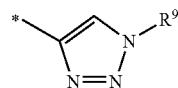

group) wherein * indicates a point of attachment to an adjacent carbon, and

R⁹ is a residue of a biomolecule having an azide group.

A method for the synthesis of the bisconjugate of Formula III includes reacting the regioisomers of Formula II with an azide-containing biomolecule.

An article or formulation includes the regioisomer of Formula III, preferably Formula IIIa, more preferably Formula IIIb, or a pharmaceutically acceptable salt thereof.

The article or formulation including the regioisomer of Formula III, preferably Formula IIIa, more preferably Formula IIIb, or a pharmaceutically acceptable salt thereof, can be used in imaging, or imaging, diagnosis, or treatment of a patient.

A bisconjugate of Formula VII is disclosed, including a regioisomer of Formula VII

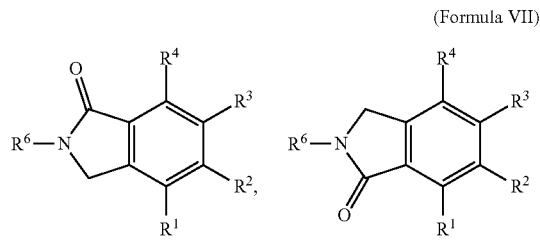

(Formula VII)

or a pharmaceutically acceptable salt thereof, wherein in Formula VII

R¹ to R⁴ are each independently hydrogen, halogen, cyano, nitro, —$C_1$-$C_6$alkyl-$C_0$-$C_6$alkyl($C_3$-$C_7$cycloalkyl), —$C_0$-$C_6$alkyl(heterocycloalkyl), $C_0$-$C_6$alkyl(aryl), or —$C_0$-$C_6$alkyl(heteroaryl), wherein groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl;

at least one of R¹ to R⁴ is —COOR¹⁰;

R⁶ is a residue of a biomolecule; and

R¹⁰ is —$C_0$-$C_{10}$alkyl moiety containing a

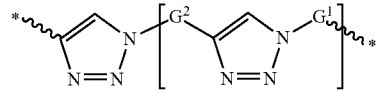

structural unit, or —$C_0$-$C_{10}$alkyl-$C_2$-$C_{10}$alkenyl moiety containing a

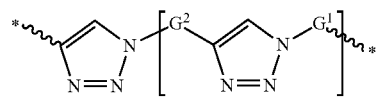

structural unit, wherein $G^1$ is a $C_1$-$C_{18}$ moiety optionally including an O, S, N, P, Si heteroatom or a combination thereof and having a valence y wherein ∿∿* indicates x number of attachments to an adjacent atom of the polymer or a terminal group of the polymer, and $G^2$ is a $C_1$-$C_{18}$ moiety optionally including an O, S, N, P, Si heteroatom or a combination thereof and having a valence x, wherein **∿∿ indicates y number of attachments to the alkyl or alkenyl moiety of $R^{10}$, the phenyl ring of the linker in the conjugate, an adjacent atom of the polymer, or a terminal group of the polymer.

A method of synthesizing the polymer of Formula VII includes reacting a bisconjugate of Formula III with a multifunctional alkyne comonomer of Formula IV and a multifunctional azide comonomer of Formula V under conditions effective for cycloaddition. In a preferred aspect, the cycloaddition is catalyzed by copper in a copper-containing paint disposed on a substrate.

An article includes a substrate; and the polymer of Formula VII or a pharmaceutically acceptable salt thereof bound to a surface of the substrate. The article can be of use in drug delivery, imaging, or a diagnosis of a condition. In another aspect, the article can further include a copper-containing paint layer between the surface of the substrate and the polymer of Formula VII or a pharmaceutically acceptable salt thereof, wherein the polymer of Formula VII or a pharmaceutically acceptable salt thereof is bound to a surface of the copper-containing paint on a side opposite the substrate.

An article includes a substrate; a layer including a copper-containing paint disposed on the substrate; and the polymer of Formula VII or a pharmaceutically acceptable salt thereof of bound to the layer of the copper-containing paint on a side opposite the substrate. In an aspect, the article is for drug delivery, imaging, or a diagnosis of a condition.

A method of treating a patient in need of treatment with an active agent includes administering to the patient an effective amount of the bisconjugate of Formula III, preferably a bisconjugate of Formula IIIa or IIIb, or a pharmaceutically acceptable salt thereof, wherein $R^6$ is a residue of a protein or antibody and $R^9$ is a residue of an active agent effective for the treatment; or administering to the patient an effective amount of the article including the polymer of Formula VII or a pharmaceutically acceptable salt thereof wherein $R^6$ is a residue of a protein or antibody effective for the treatment.

A method of treating a patient in need of treatment with an active agent includes administering to the patient an effective amount of an article including a substrate; a layer including a copper-containing paint disposed on the substrate; and the polymer of Formula VII or a pharmaceutically acceptable salt thereof bound to the layer of the copper-containing paint on a side opposite the substrate, wherein $R^6$ is a residue of a protein or antibody effective for the treatment.

A method of imaging or diagnosing a patient includes administering to the patient in need of imaging or diagnosing an effective amount of an article including a substrate; a layer including a copper-containing paint disposed on the substrate; and the polymer of Formula VII or a pharmaceutically acceptable salt thereof bound to the layer of the copper-containing paint on a side opposite the substrate, wherein $R^6$ is a residue of a protein or antibody effective for imaging or diagnosis.

The above-described and other features are exemplified by the following Figures, Detailed Description, Examples, and Claims.

BRIEF DESCRIPTION OF DRAWINGS

This patent or application file contains at least one drawing executed in color. Copies of this patent or patent application publication with color drawing(s) will be provided by the Office upon request and payment of the necessary fee.

The following Figures are exemplary aspects, which are provided to illustrate this disclosure. The Figures are not intended to limit devices made in accordance with the disclosure to the materials, conditions, or process parameters set forth herein. In the Figures.

DETAILED DESCRIPTION

Figure 1:
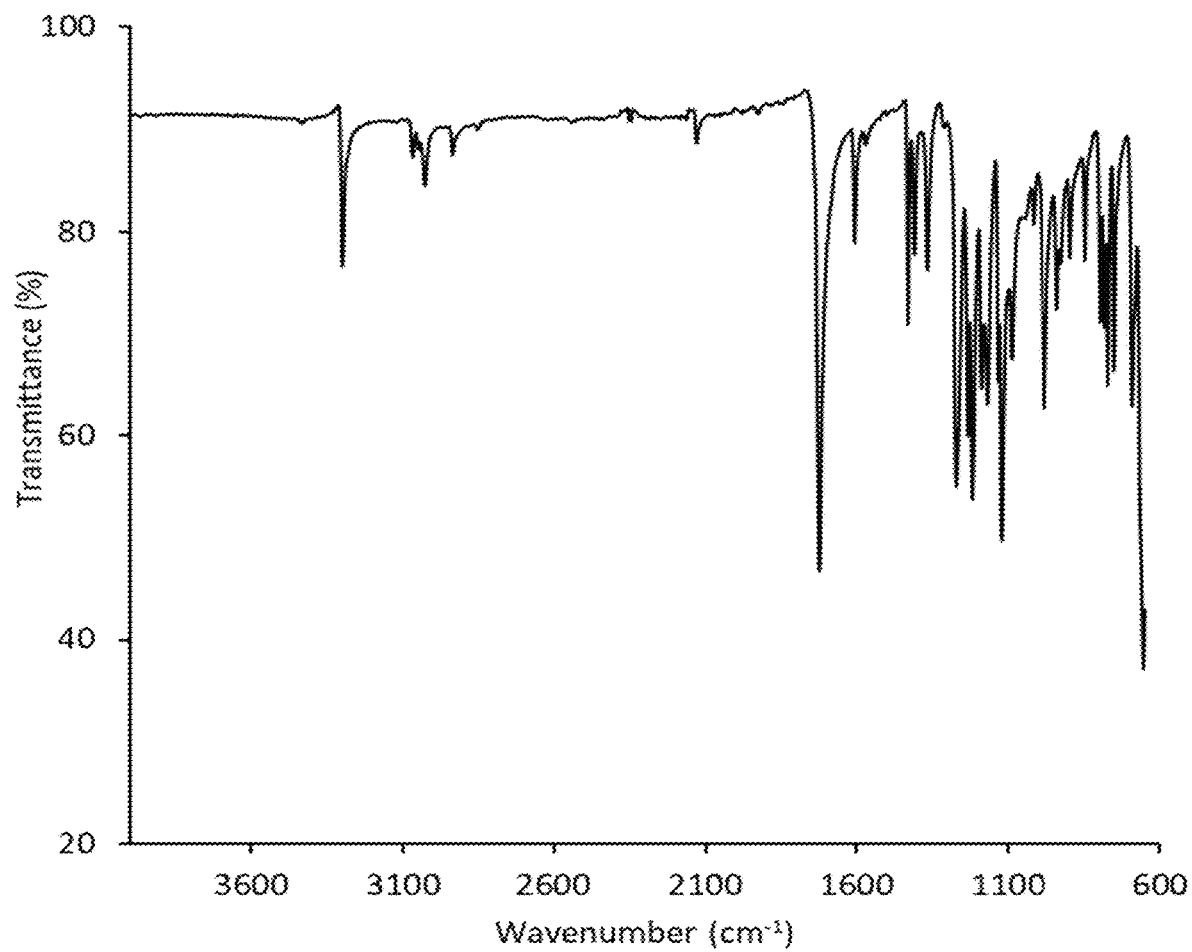
FIG. 1 is an FTIR spectrum of compound 3b.

A bifunctional linker is disclosed that is particularly useful as a bioconjugative moiety for amines such as lysine, and thus proteins containing lysine residues. The bifunctional linker can be used to link two disparate entities, for example a protein and an active agent, or a protein and an adhesive polymer. The adhesive polymer can be used to bond the first entity to a surface, allows the immobilization of biological entities such as proteins to a wide variety of surface types, conformations, and sizes.

One functionality of the bifunctional linker is provided by an ortho-phthaldialdehyde (oPA) moiety. The oPA moiety reacts selectively with a primary amine, for example the primary amines in lysine residues, to irreversibly form isoindolinones that are robust to most physiological conditions. This oPA-containing linker is especially useful due to rapid reaction rates, high conversions, and the natural abundance of lysine residues in proteins. The conjugate formed by the amine-containing compound, e.g., a protein, can then be reacted via the second functionality.

The second functionality is provided by an alkyne moiety covalently bound to the benzene ring of the oPA-containing linker. Alkynes can be used in Huisgen 1,3-dipolar cycloadditions to provide a five-membered heterocycle. Accordingly, the alkyne allows copper-catalyzed, azide-alkyne cycloadditions (CuAACs) that forms triazoles. The cycloadditions are advantageous in that the reaction is orthogonal to most naturally-occurring functional groups. Any compound or substance that contains, or can be derivatized to contain an azide, can accordingly be linked to the compound or substance including the primary amine. The cycloadditions further exhibit high chemoselectivity, and are attractive for use with proteins.

In another advantageous feature, the cycloaddition, in particular the CuAAC, can be carried out in the presence of a multifunctional alkyne comonomer and a multifunctional azide comonomer to form a triazole-containing polymer. The polymer can bond to various surfaces, allowing the primary amine-containing group to be bound to the surface vis the bifunctional linker. However, in still another advantageous feature, CuAACs can be carried out heterogeneously on various surfaces where a catalytic copper moiety is bound to a surface. Such surfaces have included copper-in-charcoal, copper nails, brass, copper nanoparticles, and other supporting structures containing copper-chelated motifs. These particular surfaces are of limited utility in the binding or immobilization of biomolecules such as proteins. The inventors hereof have discovered that a copper-containing paint can be used as the catalyst for CuAACs, where the triazole-containing polymers formed by the CuAACs can in turn be effective adhesives for the copper-containing paint, allowing binding directly to the paint. The bifunctional linkers disclosed herein can accordingly be used to bond proteins to an adhesive polymer network. This approach is a random polymerization that chain terminates with a protein or results in protein crosslinking, and is not a "grafting to" or "grafting from" method. The adhesive polymer network is in turn adheres to any surface covered with the copper-containing paint. The fast reaction rates of CuAACs limit protein diffusion before significant polymerization and surface adhesion occurs. This method of immobilizing proteins is easy, rapid, high-yield, and enables adhesion to a wide range of substrates with minimal loss in bioactivity.

The bifunctional linker for use in the method is an oPA-containing compound that includes an alkyne ester moiety. Without being bound by theory, it is believed that directly linking an electron-withdrawing group, i.e., the ester moiety, directly to the benzene ring provides an electron-poor group that can enable CuAACs to proceed even the presence of a copper (II) catalyst. The bifunctional linker is of Formula I,

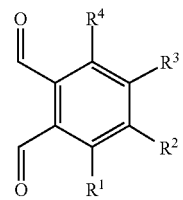

Formula I wherein in Formula I,
$R^1$ to $R^4$ are each independently hydrogen, halogen, cyano, nitro, —COOR$^5$, —$C_1$-$C_6$alkyl, —$C_0$-$C_6$alkyl ($C_3$-$C_7$cycloalkyl), —$C_0$-$C_6$alkyl(heterocycloalkyl), $C_0$-$C_6$alkyl(aryl), $C_0$-$C_6$alkyl(aryl)$C_1$-$C_6$alkyl, or —$C_0$-$C_6$alkyl(heteroaryl), wherein groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl, and
at least one of $R^1$ to $R^4$ is —COOR$^5$; and
$R^5$ is —$C_0$-$C_{10}$alkyl($C_2$-$C_{10}$alkynyl), or —$C_0$-$C_{10}$alkyl-$C_2$-$C_{10}$alkenyl($C_2$-$C_{10}$alkynyl). Preferably in Formula I, $R^5$ contains a terminal alkyne, i.e., $R^5$ is —$C_1$-$C_{10}$alkyl($C_2$alkynyl), or —$C_1$-$C_{10}$alkyl-$C_2$-$C_{10}$alkenyl ($C_2$alkynyl).

Location of the alkyne moiety at $R^3$ provides a starting material that is readily available by common synthetic methods. Accordingly, in another aspect, the bifunctional linker of Formula I is a compound of Formula Ia

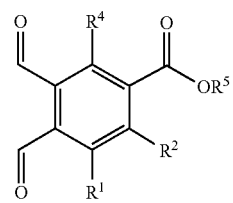

(Ia)

wherein in Formula Ia,
$R^1$, $R^2$, and $R^4$ is each independently hydrogen, halogen, cyano, nitro, —$C_1$-$C_6$alkyl, —$C_0$-$C_6$alkyl($C_3$-$C_7$cycloalkyl), —$C_0$-$C_6$alkyl(heterocycloalkyl), —$C_0$-$C_6$alkyl(aryl), or —$C_0$-$C_6$alkyl(heteroaryl), wherein the foregoing groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl;
$R^3$ is —COOR$^5$; and
$R^5$ is —$C_1$-$C_{10}$alkyl(alkynyl), or —$C_1$-$C_{10}$alkyl-$C_1$-$C_{10}$alkenyl($C_1$-$C_{10}$alkynyl). Preferably in this aspect, $R^5$ is —$C_1$-$C_6$alkyl(alkynyl) or —$C_1$-$C_6$alkyl-$C_1$-$C_{10}$alkenyl(alkynyl).

In still another aspect in Formula Ia, $R^1$, $R^2$, and $R^4$ is each independently hydrogen or $C_1$-$C_6$alkyl optionally substituted with halogen, cyano, nitro, $C_3$-$C_7$cycloalkyl, or $C_6$-$C_{12}$aryl;
$R^3$ is —COOR$^5$; and
$R^5$ is —$C_1$-$C_{10}$alkyl($C_2$-$C_{10}$alkynyl), preferably —$C_1$-$C_6$alkyl(alkynyl).

In another aspect, in the bifunctional linker of Formula I, $R^1$, $R^2$, and $R^4$ is each hydrogen;
$R^3$ is —COOR$^5$; and
$R^5$ is $C_1$-$C_4$alkyl($C_2$alkynyl).

In still another aspect, the bifunctional linker of Formula I is of Formula Ib.

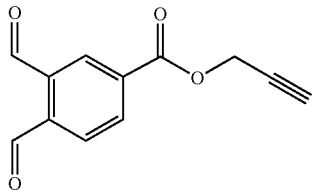

The compounds of Formula I can be readily synthesized by methods known in the art, from commercial or readily available starting materials or from commercial or readily available intermediates. While methods of synthesis are shown below, it is to be understood that each intermediate and the compounds of Formula I can be obtained by other synthetic methods, including alternative reaction conditions, particularly where large quantities are desired. The methods are accordingly not limited to the following method descriptions.

In an aspect, a process of synthesizing the compound Formula I includes: reacting a dimethylarylcarboxylic acid of Formula 1

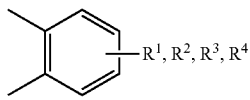

wherein $R^1$, $R^2$, $R^3$, and $R^4$ are as defined in Formula I except that at least one of $R^1$, $R^2$, $R^3$, and $R^4$ is —COOH, with a halogenating agent to provide a tetrahalomethylarylcarboxylic acid of Formula 2

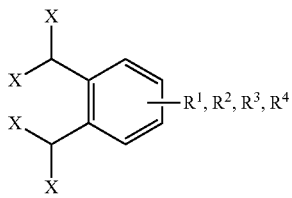

wherein $R^1$, $R^2$, $R^3$, and $R^4$ are as defined in Formula I, except that at least one of $R^1$, $R^2$, $R^3$, and $R^4$ is —COOH, and X is a halide, preferably chlorine or bromine. Halogenation can be carried out on the acid or salt form of the dimethylarylcarboxylic acid of Formula 1, depending on the halogenating agent used.

The tetrahalomethylarylcarboxylic acid (or salt thereof) of Formula 2 can be reacted with an alkyne compound having a leaving group to afford a carboxylate ester of Formula 3

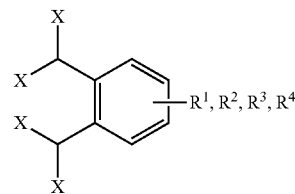

wherein $R^1$, $R^2$, $R^3$, $R^4$, and $R^5$ are as defined in Formula I, and X is a halide, preferably chlorine or bromine. The carboxylate ester of Formula 3 can be oxidized to afford the dialdehyde compound of Formula I.

For example, in an aspect, the compounds of Formula Ia can be synthesized as shown in Scheme 1.

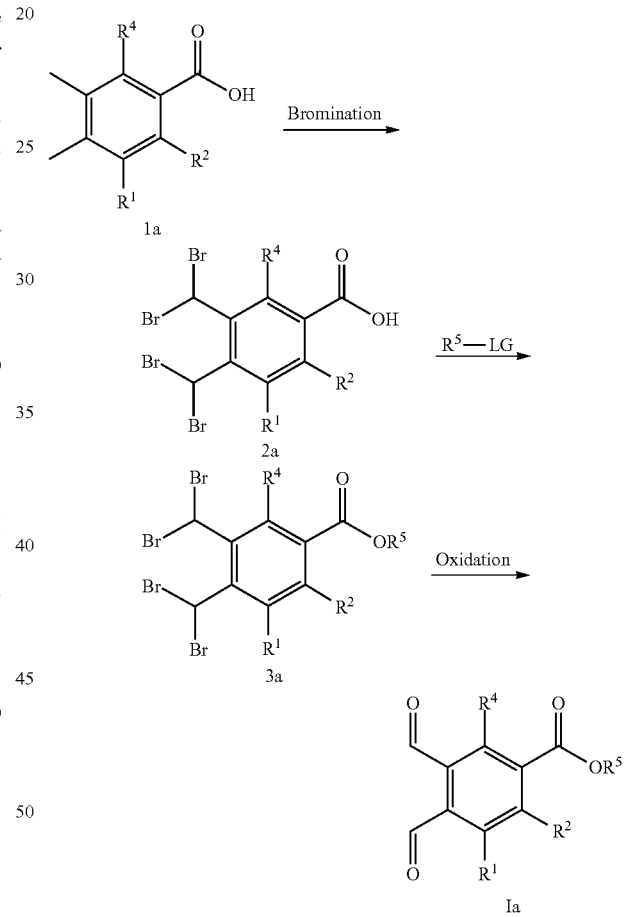

As shown in Scheme 1, starting from a dimethylarylcarboxylic acid 1a, using a suitable halogenation method, for example a bromination method, a tetrabrominated acid 2a can be prepared. The acid or the salt of the tetrabrominated acid 2a can be subjected to alkylation using an alkyne with a leaving group (LG), for example a brominated alkyne compound corresponding to $R^5$—Br to provide an ester 3a. The ester 3a can be subsequently oxidized with a suitable oxidizing agent to afford a compound of Formula Ia.

The bifunctional linker of Formula Ib is synthesized in three steps from readily available starting materials as shown in Scheme 2.

(Scheme 2)

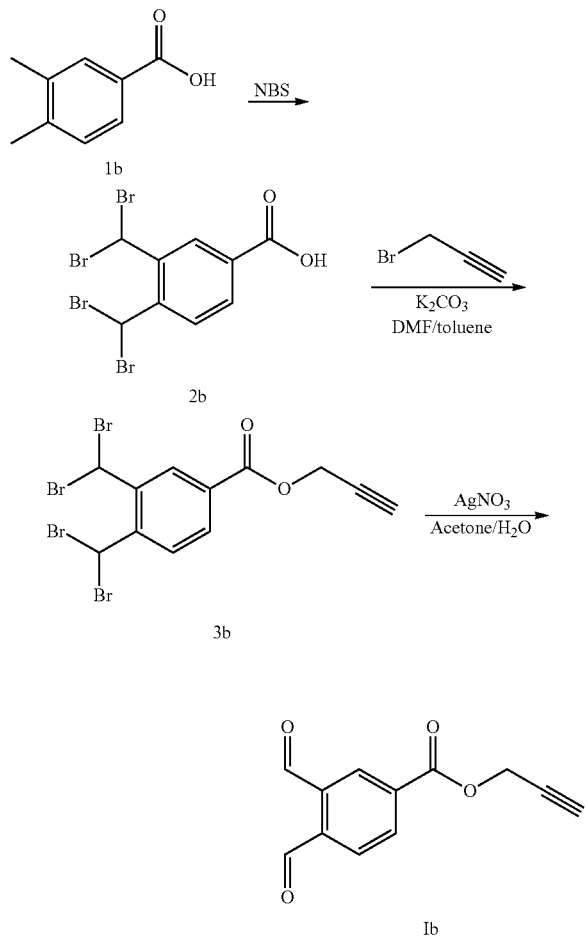

As shown in Scheme 2, starting from an inexpensive dimethylbenzoic acid 1b, a known tetrabromination technique using NBS under standard conditions yields tetrabrominated acid 2b (see, Statsuk, A. V., et al. Tuning a Three-Component Reaction For Trapping Kinase Substrate Complexes. *Journal of the American Chemical Society* 2008,130 (51), 17568-17574).

Tetrabrominated acid 2b is reacted with propargyl bromide in the presence of sodium bromide a solvent (DMF/toluene) to provide the propargyl ester 3b. Other conditions for reaction can be used, such as the reaction tetrabrominated acid 2 with propargyl bromide in the presence of sodium bicarbonate in DMF as a solvent.

Propargyl ester 3b is oxidized with silver nitrate to bifunctional linker Ib. Compound Ib is soluble in DMSO or methanol but has limited solubility in hexanes or water.

As stated above, the bifunctional linker of Formula I, preferably Formula Ia or Formula Ib, can be reacted with a primary amine via the dialdehyde group. Advantageously, the primary amine is a component of a biomolecule, for example an active agent, a peptide, a biomarker, or a protein. Specific examples of biomolecules are cytochrome c, lysozyme c, ribonuclease A, myoglobin, and bovine serum albumin (BSA). The reaction product is a conjugate wherein two regioisomers of Formula II may be formed,

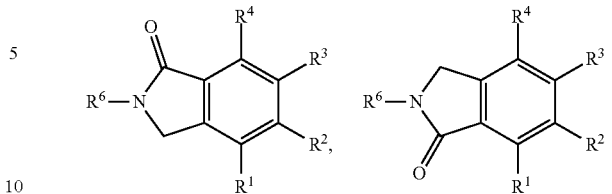

or a pharmaceutically acceptable salt thereof, wherein in Formula II, $R^1$ to $R^4$ are each as defined in Formula I, and $R^6$ is a residue of the biomolecule, for example a residue of an active agent, a peptide, a biomarker, or a protein including the primary amino group. In an aspect, $R^6$ is a residue of a lysine in a peptide or in a protein. It is to be understood that reference herein to "a regioisomer" of a given Formula may include one regioisomer or both regioisomers.

In another aspect, in Formula II,
  $R^1$, $R^2$, and $R^4$ is each independently hydrogen, halogen, cyano, nitro, —$C_1$-$C_6$alkyl, —$C_0$-$C_6$alkyl($C_3$-$C_7$cycloalkyl), —$C_0$-$C_6$alkyl(heterocycloalkyl), —$C_0$-$C_6$alkyl(aryl), or —$C_0$-$C_6$alkyl(heteroaryl), wherein the foregoing groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl;
  $R^3$ is —$COOR^5$;
  $R^5$ is —$C_1$-$C_{10}$alkyl(alkynyl), or —$C_1$-$C_{10}$alkyl-$C_1$-$C_{10}$alkenyl($C_2$-$C_{10}$alkynyl); and
  $R^6$ is a biomolecule residue, preferably a protein residue. Preferably in this aspect, $R^5$ is —$C_1$-$C_6$alkyl(alkynyl) or —$C_1$-$C_6$alkyl-$C_1$-$C_{10}$alkenyl(alkynyl).

In still another aspect, the regioisomer can be of Formula IIa

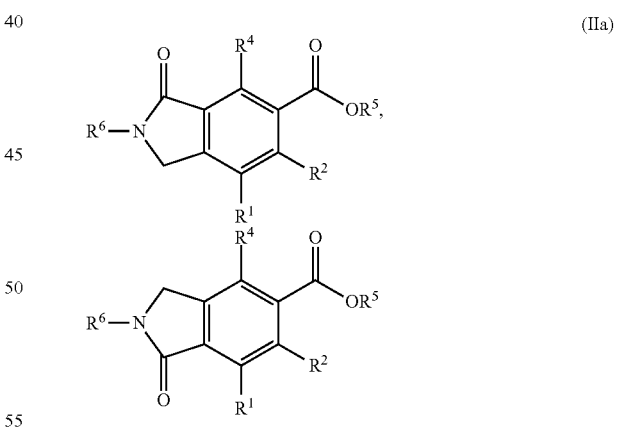

or a pharmaceutically acceptable salt thereof, wherein
  $R^1$, $R^2$, and $R^4$ is each independently hydrogen or $C_1$-$C_6$alkyl;
  $R^5$ is —$C_1$-$C_{10}$alkyl($C_2$-$C_{10}$alkynyl), preferably —$C_1$-$C_6$alkyl($C_2$alkynyl); and
  $R^6$ is a protein residue.
In another aspect, in the conjugate of Formula II,
  $R^1$, $R^2$, and $R^4$ is each hydrogen;
  $R^3$ is —$COOR^5$;
  $R^5$ is $C_1$-$C_4$alkyl($C_2$alkynyl); and
  $R^6$ is a lysine residue of a protein.

In still another aspect, the regioisomers are of Formula IIb

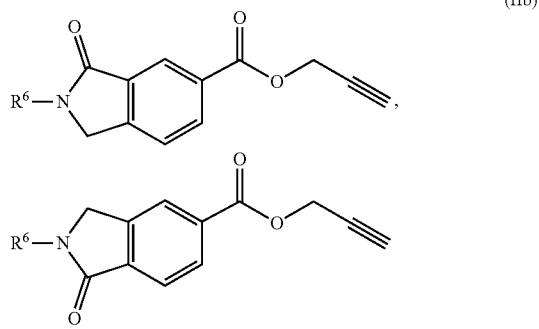

(IIb)

or a pharmaceutically acceptable salt thereof, wherein $R^6$ is a residue of a lysine of a protein.

Conditions for formation of the conjugate of Formula II are known, and can vary depending on the particular biomolecule used. For example, the components of the reaction can be combined in a suitable solvent such as water or a combination of water and a miscible organic solvent such as DMSO, THF, or the like. Reaction can proceed at room temperature, optionally in the presence of a buffer, such as a borate buffer, to maintain alkaline conditions.

The second functionality of the bifunctional linker is then reacted with a second entity, e.g., a biomolecule such as an active agent, a biomarker, or a comonomer, by cycloaddition to provide a bisconjugate. In particular, the conjugate of Formula II is subjected to an azide-alkyne cycloaddition, where the second entity includes an azide functionality. The resultant bisconjugate includes a triazole group as shown in Scheme 3

(Scheme 3)

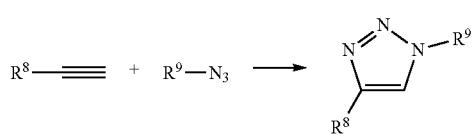

wherein $R^8$ represents the bifunctional linker conjugated to the first entity, and $R^9$ represents the second entity, e.g., a biomolecule having or derivatized with an azide.

In an aspect, the second entity is a biomolecule, for example a compound such as an active agent or biomarker molecule derivatized with an azide. Cycloaddition provides regioisomers of Formula III (III)

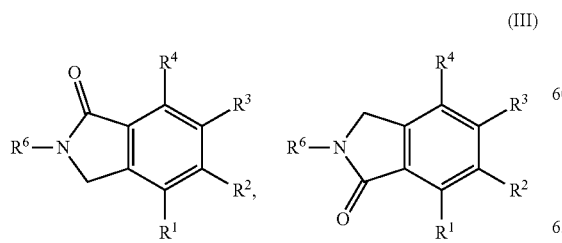

or a pharmaceutically acceptable salt thereof, wherein in Formula III $R^1$ to $R^4$ are each independently hydrogen, halogen, cyano, nitro, —$C_1$-$C_6$alkyl, —$C_0$-$C_6$alkyl($C_3$-$C_7$cycloalkyl), —$C_0$-$C_6$alkyl(heterocycloalkyl), $C_0$-$C_6$alkyl(aryl), or —$C_0$-$C_6$alkyl(heteroaryl), wherein groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl;

at least one of $R^1$ to $R^4$ is —$COOR^7$; and $R^7$ is —$C_0$-$C_{10}$alkyl($C_2$-$C_{10}$ moiety containing a

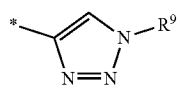

group), or —$C_0$-$C_{10}$alkyl-$C_2$-$C_{10}$alkenyl($C_2$-$C_{10}$ moiety containing a

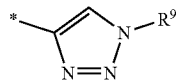

group) wherein * indicates a point of attachment to an adjacent carbon and $R^9$ is a residue of the biomolecule having an azide group.

Preferably in Formula III, the $R^7$ group is derived from a terminal alkyne, i.e., $R^7$ is —$C_1$-$C_{10}$alkyl(

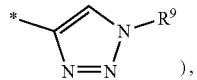

), or —$C_1$-$C_{10}$alkyl-$C_2$-$C_{10}$alkenyl (

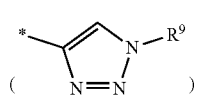

)

wherein * indicates a point of attachment to an adjacent carbon atom and $R^9$ is a residue of the biomolecule having an azide group.

In another aspect, the regioisomers are of Formula IIIa (IIIa)

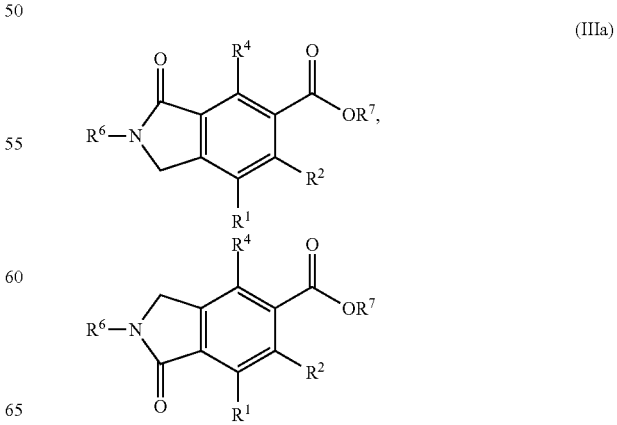

or a pharmaceutically acceptable salt thereof, wherein
$R^1$, $R^2$, and $R^4$ is each independently hydrogen or $C_1$-$C_6$alkyl;
$R^7$ is —$C_1$-$C_{10}$alkyl($C_2$-$C_{10}$ moiety containing a

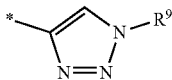

group), preferably —$C_1$-$C_6$alkyl(

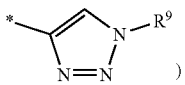 )

wherein * indicates a point of attachment to an adjacent carbon atom and $R^9$ is a residue of the biomolecule having an azide group.

In another aspect, in the regioisomers of Formula III
$R^1$, $R^2$, and $R^4$ is each hydrogen;
$R^3$ is COOR$^7$,
$R^7$ is $C_1$-$C_4$alkyl(and $R^9$ is a residue of the biomolecule having an azide group) wherein * indicates a point of attachment to an adjacent carbon atom; and
$R^6$ is a protein residue, preferably a lysine residue of a protein.

In still another aspect, the regioisomers are of Formula IIIb

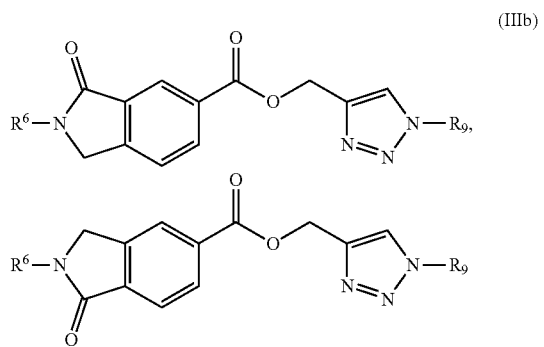

(IIIb)

or a pharmaceutically acceptable salt thereof, wherein $R^6$ is a residue of a lysine of a protein and $R^9$ is a residue of the biomolecule having an azide group.

Methods for carrying out the cycloadditions to provide the bisconjugates of Formula III are known in the art. In an aspect, no catalyst need be present. In another aspect, the cycloadditions are copper-catalyzed azide-alkyne cycloadditions (CuAACs), which are most commonly catalyzed by copper(I) salts or complexes, but can also be catalyzed by copper(II) and copper(0) salts or complexes under appropriate conditions. Exemplary catalysts include, for example CuI, CuSO$_4$, copper metal, Cu-powder, CuBr, CuCl, Cu(OAc)$_2$, CuBr(Ph$_3$P)$_3$, [Cu(CH$_3$CN)$_4$]PF$_6$, CuBr$_2$/Pd (OAc)$_2$, CuCl/Pd(dba)$_2$, CuOtriflate (CuOTf), Cu(CH$_3$CN)$_4$ OTf, or a combination thereof; and a ligand, for example, tris((1-benzyl-4-triazolyl)methyl)amine (TBTA), N,N,N', N'',N''-pentamethyldiethylenetriamine (PMDETA), 2,2'-Bipyridine (bipy), bathophenanthroline, or a combination thereof. A suitable copper salt or complex includes example, copper (I) iodide (CuI), anhydrous copper sulfate (CuSO$_4$), copper sulfate pentahydrate (CuSO$_4$.5H$_2$O), copper metal, CuCl, CuAl$_2$O$_4$, copper on carbon, or a combination thereof.

The cycloaddition or the CUAAC can be carried out in a variety of solvents, for example tetrahydrofuran (THF), pyridine, dimethylsulfoxide (DMSO), dimethylformamide (DMF), toluene, N-methylpyrrolidone (NMP), acetonitrile (CH3CN), water, acetone, methanol (MeOH), ethanol (EtOH), isopropanol, tert-butanol, dioxane, or a combination thereof. In aspect, a combination of water and a water-miscible organic solvent can be used for CuAACs. For example, a solvent system including water and an organic solvent such as DMSO, THF, and tert-butanol (TluOH) have been used.

A reducing or an oxidizing agent, for example, sodium ascorbate (NaAsc), ascorbic acid, P(OCH$_2$CH$_3$)$_3$, triphenyl phosphine (PPh$_3$), air, in situ Cu$_2$O, or a combination thereof can be present, depending on the catalyst used. A base can be present, for example, diisopropylethylamine (DIPEA), 1,8-diazabicyclo[5.4.0]undec-7-ene (DBU), pyridine, triethylamine, or a combination thereof.

The cycloadditions can be carried out in air or an inert atmosphere (e.g., nitrogen or argon), at room temperature.

The bisconjugate of Formula III, in particular of Formula IIIa and Formula IIIb, are especially useful to form a bisconjugate of a protein or antibody with a small molecule such as an active agent or a biomarker. The protein or antibody can be selected to target a specific therapeutic site. The bisconjugates can then be used for active agent delivery, imaging, or diagnosis. For example, the bisconjugates can be used to deliver a cytotoxic active agent for anti-cancer treatment. Alternatively, the active agent can be another protein or antibody, to provide a crosslinked protein. Optionally, the protein or antibody can be derivatized with polyethylene glycol (PEGylated) to increase its lifetime in the body. Other applications include tagging for mass spectrometry analysis. When used in these applications, the bisconjugates can be in the form of an article or formulation. For example, the bisconjugates can be a component of a delivery device or an imaging article such as a test strip or a microtiter plate, or a formulation for use in an imaging device.

In another aspect, the bisconjugate of Formula III, in particular of Formula IIIa and Formula IIIb, can be a component of a formulation for administration to a patient, such as a parenteral formulation, or an oral dosage formulation such as tablet, a powder capsule, a gel capsule, or a powder as is known in the art. The dosage formulations can be timed release. The dosage formulations can include other imaging or active agents.

A method of treating a patient in need of treatment with an active agent can include administering to the patient a formulation including an effective amount of the bisconjugate of Formula III, in particular of Formula IIIa or Formula IIIb, wherein $R^6$ is a protein or antibody, and $R^9$ is the active agent, optionally wherein bisconjugates is in the form of a formulation. A method of imaging or diagnosing a patient can include administering to the patient a formulation including an effective amount of the bisconjugate of Formula III, in particular of Formula IIIa or Formula IIIb, are wherein $R^6$ is a protein or antibody, and $R^9$ is a biomarker or imaging agent.

In another aspect, the conjugate of Formula II is reacted to provide an adhesive polymer covalently linked to the bifunctional linker. Again, the reaction is an alkyne-azide cycloaddition, preferably copper-catalyzed, and carried out in the presence the conjugate of Formula II and two different comonomers, one comonomer containing two or more alkyne groups, and the other comonomer containing two or more azide groups. Cycloaddition forms a polymer moiety containing triazole groups. The triazole groups can be effective to bind the bisconjugate to the painted surface.

The comonomer including at least two alkyne groups can be of Formula IV

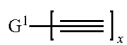  (IV)

wherein $G^1$ is a $C_1$-$C_{18}$ moiety optionally including an O, S, N, P, Si heteroatom or a combination thereof and having a valence x; and x is the number of terminal alkyne groups and is 2 or greater, for example 2 to 6.

The group $G^1$ is not particularly limited, and can be linear or cyclic, saturated, unsaturated, or aromatic, and with or without one or more functional groups such as halogen, cyano, nitro, hydroxy, cyano, carboxylic acid, or carboxylic ester.

In an aspect, $G^1$ is a $C_2$-$C_{12}$ moiety optionally including an O or S atom, and x is 2 to 4.

In another aspect, the comonomer including at least two alkyne groups is of Formula IVa

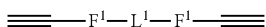  (IVa)

wherein in Formula IVa each $F^1$ is independently the same or different functional group, for example —O—, —S—, —C(=O)—, —C(=O)O—, or —OC(=O)—, and $L^1$ is a divalent $C_1$-$C_{12}$ hydrocarbon, for example $C_1$-$C_6$alkyl, $C_3$-$C_7$cycloalkyl, -, or $C_6$-$C_{12}$aryl, each optionally substituted with halogen, cyano, nitro, or cyano.

In an aspect in Formula IV, each $F^1$ is an ester group, and $L^1$ is an ethylene group, to provide a dialkyne of the Formula IVb.

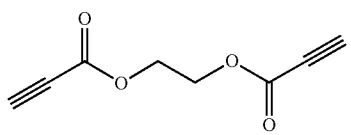  (IVb)

The comonomer including at least two azide groups can be of Formula V

  (V)

wherein in Formula V $G^2$ is a $C_1$-$C_{18}$ moiety optionally including an O, S, N, P, Si heteroatom or a combination thereof and having a valence y; and y is the number of azide groups and is 2 or greater, for example 2 to 6.

The group $G^2$ is not particularly limited, and can be linear or cyclic, saturated, unsaturated, or aromatic, and with or without one or more functional groups such as cyano, nitro, hydroxy, carboxylic acid, or carboxylic ester.

In an aspect, $G^2$ is a $C_2$-$C_{12}$ moiety optionally including an O or S atom, and y is 2 to 4.

In another aspect, the comonomer including at least two azide groups is of Formula Va $$N_3\text{—}CH_2\text{-}L^2\text{-}CH_2\text{—}N_3 \quad (Va)$$

wherein in Formula (Va), $L^2$ is a divalent $C_1$-$C_{12}$ hydrocarbon, for example $C_1$-$C_6$alkyl, $C_3$-$C_7$cycloalkyl, or —$C_6$-$C_{12}$aryl, each optional substituted with cyano, nitro, hydroxy, cyano, —(CH$_2$)OH, carboxylic acid, or carboxylic ester.

In an aspect in Formula Va, $L^2$ is carbon substituted with two —(CH$_2$)OH groups, to provide a diazide of the Formula Vb.

  (Vb)

As stated above, cycloaddition of these two comonomers provides a polymer that includes triazole groups. For example, cycloaddition of the comonomer including at least two alkyne groups of Formula IV and the comonomer including at least two azide groups of Formula V provides a polymer including structural units (VI)

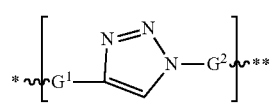  (VI)

wherein $G^1$ and $G^2$ are as defined in Formulas IV and V, *〰 indicates x number of attachments to an adjacent atom of the polymer or a terminal group of the polymer, and 〰** indicates y number of attachments to an adjacent atom of the polymer or a terminal group of the polymer. Where more than two alkyne or azide groups are present in the comonomers, the polymer will not be linear. Cycloaddition, in particular CuAAC, of a conjugate of a regioisomers of Formula III in the presence of the comonomer including two alkyne groups of Formula IVa and the comonomer including two azide groups of Formula Va accordingly provides polymers including a regioisomer of Formula VII Formula VII

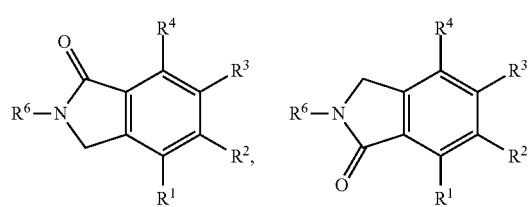

or a pharmaceutically acceptable salt thereof, wherein in Formula VII $R^1$ to $R^4$ are each independently hydrogen, halogen, cyano, nitro, —$C_1$-$C_6$alkyl, —$C_0$-$C_6$alkyl($C_3$-$C_7$cycloalkyl), —$C_0$-$C_6$alkyl(heterocycloalkyl), $C_0$-$C_6$alkyl(aryl), or —$C_0$-$C_6$alkyl(heteroaryl), wherein groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl;

at least one of $R^1$ to $R^4$ is —COOR$^{10}$;

$R^6$ is a residue of a biomolecule; and $R^{10}$ is —$C_0$-$C_{10}$alkyl moiety containing a

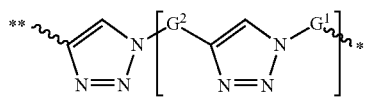

structural unit, or —$C_0$-$C_{10}$alkyl-$C_2$-$C_{10}$alkenyl moiety containing a

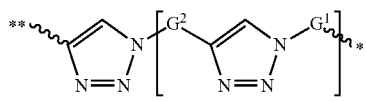

structural unit, wherein $G^1$ and $G^2$ are as defined in Formula IV and Formula V, ** ∿∿∿ indicates y number of attachments to the alkyl or alkenyl moiety of $R^{10}$, the phenyl ring of the linker in the conjugate, an adjacent atom of the polymer the polymer, or a terminal group of the polymer, and ∿∿∿ * indicates x number of attachments to an adjacent atom of the polymer or a terminal group of the polymer.

Similar polymers can be obtained by cycloaddition, in particular CuAAC of a conjugate of a regioisomer of Formula IIIa or Formula IIIb in the presence of the comonomers including two alkyne groups of Formula IV and the comonomer including two azide groups of Formula V. Such polymers will also contain crosslinks.

On the other hand, cycloaddition of the comonomers including two alkyne groups of Formula IVa and the comonomer including two azide groups of Formula (Va) provides a polymer including linear structural units (VIa)

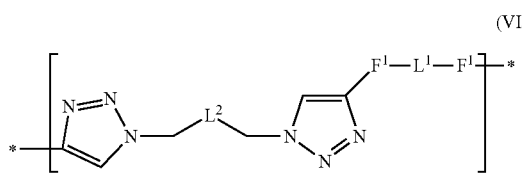

(VIa)

wherein $F^1$, $L^1$, and $L^2$ are as defined in Formulas (IVa) and (Va) and * is a point of attachment to an adjacent atom or terminal group of the polymer. Cycloaddition, in particular CuAAC of a conjugate of a regioisomer of Formula III in the presence of the comonomer including two alkyne groups of Formula IVa and the comonomer including two azide groups of Formula Va accordingly provides regioisomers of polymers of Formula VIIa

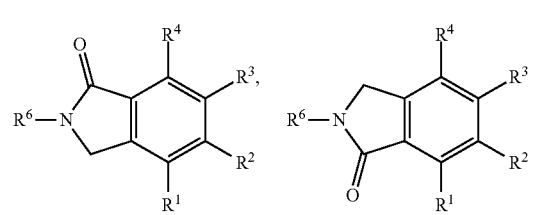

VIIa or a pharmaceutically acceptable salt thereof, wherein in Formula VIIa $R^1$ to $R^4$ are each independently hydrogen, halogen, cyano, nitro, —$C_1$-$C_6$alkyl, —$C_0$-$C_6$alkyl($C_3$-$C_7$cycloalkyl), —$C_0$-$C_6$alkyl(heterocycloalkyl), $C_0$-$C_6$alkyl(aryl), or —$C_0$-$C_6$alkyl(heteroaryl), wherein groups except hydrogen, halogen, cyano, and nitro are optionally substituted with halogen, cyano, nitro, a $C_1$-$C_6$alkyl, a $C_3$-$C_7$cycloalkyl, a heterocycloalkyl, a heteroaryl, or an aryl, and at least one of $R^1$ to $R^4$ is —COOR$^{10}$;

$R^6$ is a residue of a biomolecule; and $R^{10}$ is a —$C_0$-$C_{10}$alkyl moiety containing a repeating

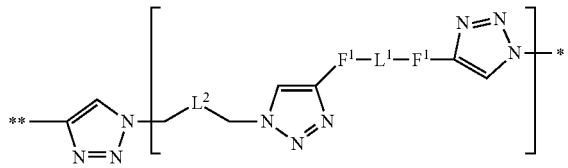

structural unit, or a —$C_0$-$C_{10}$alkyl-$C_2$-$C_{10}$alkenyl moiety containing a repeating

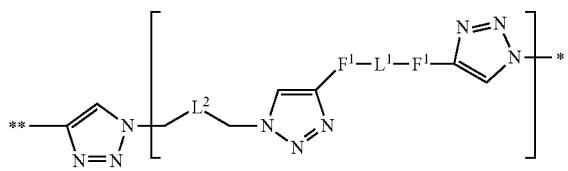

structural unit, wherein $F^1$, $L^1$, and $L^2$ are as defined in Formulas IVa and Vb, ** indicates a point of attachment to an adjacent carbon on the alkyl moiety or the alkenyl moiety of $R^{10}$ or the phenyl ring of the linker in the conjugate, and * indicates attachment to an adjacent atom of the polymer or a terminal group of the polymer. Crosslinking may occur where the biomolecule has more than one primary amine group that can react in the conjugation.

Finally, cycloaddition of the comonomer including two alkyne groups of Formula IVb and the comonomer including two azide groups of Formula Vb provides a polymer including linear structural units VIb

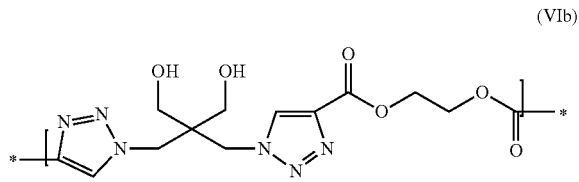

(VIb)

wherein * is a point of attachment to an adjacent atom of the polymer or a terminal group.

It is to be understood that in any of the cycloadditions carried out using comonomers having two alkyne and two azide groups, the polymer structural units are linear, but crosslinking can occur via $R^6$ groups having two more primary amines. Cycloaddition of a conjugate of a regioisomer of Formula IIIb in the presence of the comonomer including two alkyne groups of Formula IVb and the comonomer including two azide groups of Formula Vb accordingly provides a regioisomer of polymers of Formula VIIb between the polymer and the substrate. In an aspect, the article includes a substrate and the polymer of Formula VII, preferably of Formula VIIa or Formula VIIb, disposed directly on a surface of the substrate.

In a preferred aspect, a copper-containing paint can be used as the catalyst for CuAACs, where the triazole-containing polymers formed by the CuAACs can in turn be effective adhesives for the copper-containing paint, allowing for attachment directly to the paint. Use of a copper-containing paint allows the attachment of the bisconjugates to a broad variety of surface types, sizes, and configurations. Suitable paints are commercially available, and generally include copper as a chelate in the formulation.

One concern with copper(I)-based paint is that the copper may oxidize under ambient conditions, slowing the rate of the CuAAC reaction. Therefore, a reducing agent such a sodium ascorbate can be included in the reaction mixture to reduce any copper(II) back to copper(I) and to accelerate the polymerization. Electron-poor alkynes tend to undergo CuAACs more quickly, and α,β-unsaturated alkynes have previously enabled CuAACs even in the presence of copper (II).

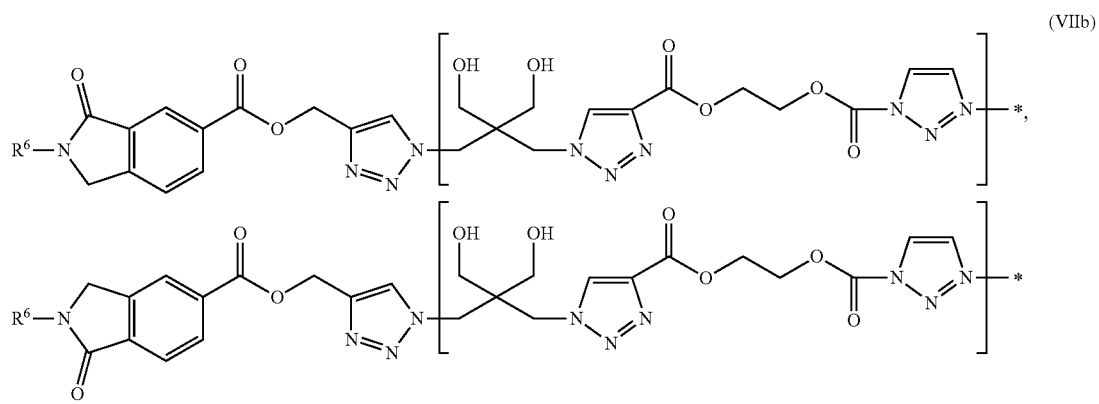

(VIIb)

or a pharmaceutical salt thereof, wherein $R^6$ is a residue of a biomolecule, and * indicates attachment to an adjacent atom of the polymer or a terminal group of the polymer. Crosslinking may occur where the biomolecule has more than one primary amine group that can react in the conjugation. In an aspect, $R^6$ is a residue of a protein having a terminal amino group. In a preferred aspect $R^6$ is a residue of a lysine of a protein.

Methods for carrying out the cycloadditions, in particular the CuAACs are similar to those described above. In an aspect, the cycloaddition can be carried out on a substrate in the absence or presence of a catalyst, for example a copper catalyst as described above. The substrate can be of any material, for example a ceramic, a polymer, a metal (such as aluminum, a metal alloy, a glass, a carbon (for example, a carbon nanomaterial), or the like. The substrate can be of any size, surface area, or configuration. A composition including the components for cycloaddition can be coated onto the substrate by any method, and allowed to react to form a polymer layer including the polymer of Formula VII, preferably of Formula VIIa or Formula VIIb. The layer can be continuous or discontinuous. The articles formed thereby include a substrate and the polymer of Formula VII, preferably of Formula VIIa or Formula VIIb disposed on a surface of the substrate. Other layers can be present, for example a primer layer or an additional adhesive layer Articles formed using a copper-containing paint accordingly include a substrate; a layer of a copper-containing paint disposed on a substrate; and a bisconjugate of Formula VII, preferably Formula VIIa and Formula VIIb, bound to the paint on a side opposite the substrate. The substrate can be of any material, for example a ceramic, a polymer, a metal, a metal alloy, a glass, a carbon (for example a carbon nanomaterial), or the like. The copper-containing paint can be in any configuration, for example continuous or discontinuous, or of any area, for example nanosized, micrometer-sized, millimeter-sized, centimeter-sized, or even larger. As used herein, "bound" can include chemical binding via a covalent bonding, ionic binding, van der Waals binding, or any other type of physical binding. Other layers can be present, in the article for example a primer layer or an additional adhesive layer between the bisconjugate and the copper paint layer, or between the copper paint layer and the substrate. In an aspect, the article includes a substrate, a layer of the copper-containing paint disposed on the substrate, and the polymer of Formula VII, preferably of Formula VIIa or Formula VIIb, disposed directly on the layer of the copper-containing paint on a side of the layer opposite the substrate.

A method of forming the article includes disposing a bifunctional compound of Formula III, preferably Formula IIIa or Formula IIIb, a multifunctional alkyne comonomer of Formula IV, preferably of Formula IVa or Formula IVb, and a multifunctional azide comonomer of Formula V, preferably of Formula Va or Formula Vb, on a copper paint disposed on a substrate, under conditions effective to provide a compound of Formula VI, preferably of Formula VIa or Formula VIb bound to the copper paint on the substrate. Conditions may be similar to those described above for cycloaddition. In an aspect, a reducing agent, e.g., ascorbic acid or a salt thereof may be present.

Proteins bound to a substrate, i.e., a solid support, have been widely used for drug delivery, imaging, in microarrays, in analytical applications such as ELISA, and the like. Incorporating the activity of proteins into coatings is a promising avenue for developing new functional materials. Use of the bifunctional linkers of Formula I to form conjugates with a protein, followed by formation of an adhesive network, provides an efficient method to rapidly apply bioactive coatings onto a wide variety of substrates. The relative thinness of the polymer matrix is an advantage for because the bound proteins are not buried in a layer of adhesive polymer, allowing them to interact more freely with the environment.

The bisconjugates of Formula VII, particularly Formula VIIa and VIIb, are also useful to conjugate a protein or antibody to a substrate for therapeutic, imaging, or diagnostic uses. The protein or antibody can be selected to target a specific therapeutic site, or for therapeutic purposes, or both. The bisconjugates can then be used for delivery to the site, followed by treatment, imaging, or diagnosis. A method of treating a patient in need of treatment with a protein or antibody active agent can include administering to the patient an effective amount of an article including the bisconjugate of Formula VII, particularly Formula VIIa or VIIb, wherein $R^6$ is a residue of protein or antibody active agent. A method of imaging or diagnosing a patient can include administering to the patient in need of imaging or diagnosis an effective amount of the bisconjugate of Formula VII, particularly Formula VIIa or VIIb, wherein $R^6$ is a residue of a protein or antibody biomarker or imaging agent.

EXAMPLES

Materials

All reagents used in the Examples were analytical grade and obtained from Alfa-Aesar, Fisher Scientific, Oakwood Chemicals, Sigma-Aldrich, Strem Chemicals, Cambridge Isotope Laboratories, or ThermoFisher Scientific and used without further purification. The following abbreviations are used, in addition to those defined elsewhere herein.

AcOH Acetic acid
BOC tert-Butoxycarbonyl
DMF Dimethylformamide
DMF-DMA Dimethylformamide-dimethylacetal
DMSO Dimethyl sulfoxide
DSC Differential scanning calorimetry
EtOAc Ethyl acetate
NBS N-Bromosuccinimide
MHz Megahertz
TGA Thermogravimetric analysis
p-TsOH p-Toluenesulfonic acid Analytical Methods Fluorescent Microscopy. A Nikon reflectance microscope was equipped with an X-Cite 120LED Boost illumination system and Hamamatsu digital CMOS camera using a TRITC filter.

Profilometry. ZETA 20 optical profiling microscope (Zeta Instruments Inc.) equipped with 20× objective lens was utilized for optical microscopy.

FTIR (Fourier transform infrared) Spectroscopy. Attenuated total reflectance-Fourier transform infrared spectroscopy was performed using a Perkin-Elmer Spectrum 100 spectrophotometer. The spectral range was selected as 4000-650 $cm^{-1}$ with a resolution of 4 $cm^{-1}$.

Thermogravimetric Analysis (TGA). Samples weighing 2-10 milligrams (mg) were heated at 10° C./min from ambient to 600° C. in a stream of nitrogen in the microbalance of a TA Instruments TGA Q5000.

Differential Scanning Calorimetry (DSC). Samples weighing 2-10 mg were heated at 10° C./min from −50° C. to 150° C. in a stream of nitrogen in the microbalance of a Mettler Toledo DSC II, and were measured on the second heating/cooling cycle.

Nuclear Magnetic Resonance (NMR) Spectroscopy. All proton decoupled $^{13}C$ and $^1H$ NMR spectra were recorded on a Bruker Avance 400 MHz spectrometer and were taken in deuterated chloroform. The signal for residual protic solvent was set at 7.26 ppm for $^1H$ NMR and the carbon signal was also set on the solvent peak at 77.16 ppm for $^{13}C$ NMR.

Mass Spectrometry (MS). High resolution mass spectra (HRMS) were obtained on a VG Analytical VG-70S mass spectrometer with electron impact (EI) ionization and analyzed by double-focusing magnetic sectors. Low resolution mass spectra (LRMS) were obtained on a Biotage Dalton 2000 Mass Detector. Protein mass spectra were collected at the University of Illinois Roy J. Carver Biotechnology Center after trypsin digestion with liquid chromatography-mass spectrometry (LC-MS).

Scanning Electron Microscopy (SEM). A Thermo Scientific Scios scanning electron microscope was used to image the particles. The samples were sputter coated with iridium to make them electrically conductive.

Ultraviolet-visible Spectroscopy (UV-Vis). A PerkinElmer Lambda 950 UV-Vis spectrometer with an InGaAs detector was used.

Example 1

This example illustrates the preparation of the bifunctional linker of Formula Ib. Prop-2-yn-1-yl 3,4-bis(dibromomethyl)benzoate (3b).

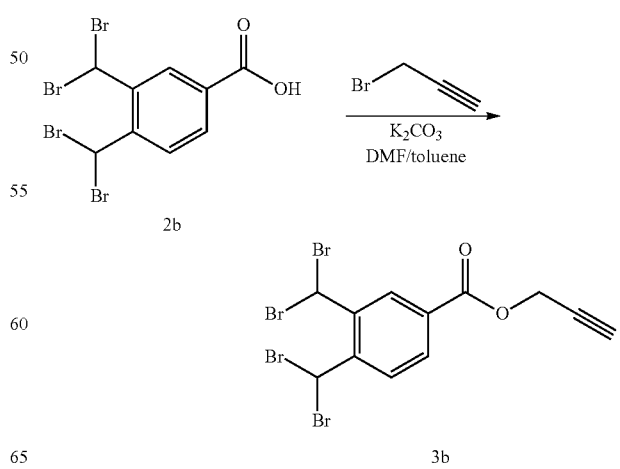

Compound 2b was prepared starting from dimethylbenzoic acid 1b using a known tetrabromination method using NBS as a brominating agent to yield tetrabrominated acid 2b (Statsuk, A. V., et al., Tuning a Three-Component Reaction For Trapping Kinase Substrate Complexes. *Journal of the American Chemical Society* 2008, 730 (51), 17568-17574). Better yields may be obtained by reacting tetrabrominated acid 2b with propargyl bromide in the presence of sodium bicarbonate in DMF only as the solvent.

In one method of proceeding, compound 3b was prepared as follows. A 100 mL round bottom flask was charged with 5 (3.99 g, 8.57 mmol), along with a magnetic stir bar and septa. The flask was purged with argon for 15 minutes. Anhydrous DMF (44 mL, 0.19 M) was added to the flask before cooling the stirring mixture in an ice bath for one hour. Propargyl bromide (1.1 mL, 10 mmol, 1.2 equiv) and sodium bicarbonate (1.44 g, 17.1 mmol, 2.00 equiv) were each added in one portion. The reaction mixture was stirred overnight and allowed to slowly come to room temperature. The reaction mixture was diluted with chloroform (100 mL), and an extraction was performed with water (100 mL, 5×) to remove the DMF. The combined organic layers were washed with brine, dried over anhydrous MgSO4, and concentrated under reduced pressure to provide a brown solid that was further purified by column chromatography ($SiO_2$:$CHCl_3$). The filtrate was concentrated with rotary evaporation to yield compound 3b as a white solid (3.02 g, 5.99 mmol, 70% yield). FIG. 1 shows the FTIR spectra of compound 3b.

$^1$H NMR (400 MHz, DMSO-$d_6$) δ: 8.36 (s, 1H), 8.06 (d, 1H, J=8.1 Hz), 8.01 (d, 1H, J=8.3 Hz), 7.80 (s, 1H), 7.77 (s, 1H), 5.01 (d, 2H, J=2.3 Hz), 3.68 (m, 1H). $^{13}$C NMR (100 MHz, $CDCl_3$) δ: 164.0, 131.6, 131.1, 77.3, 75.7, 53.2, 35.6, 35.4.

HRMS (EI) found m/z=499.7273 ($M^+$), calculated for $C_{12}H_8Br_4O_2$: 499.7258. IR v ($cm^{-1}$): 3299, 3207, 2132, 1724.

Prop-2-yn-1-yl 3,4-diformylbenzoate (Ib)

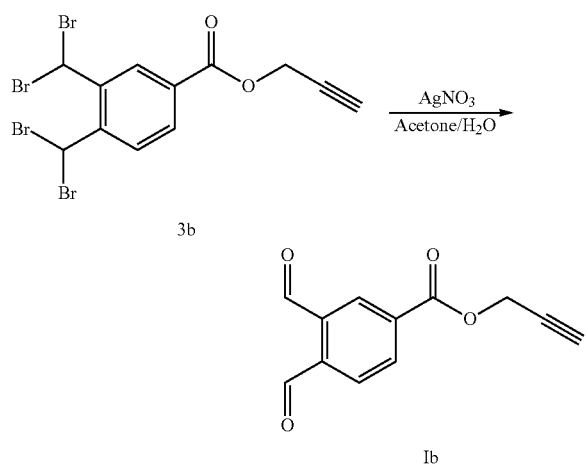

Figure 2:
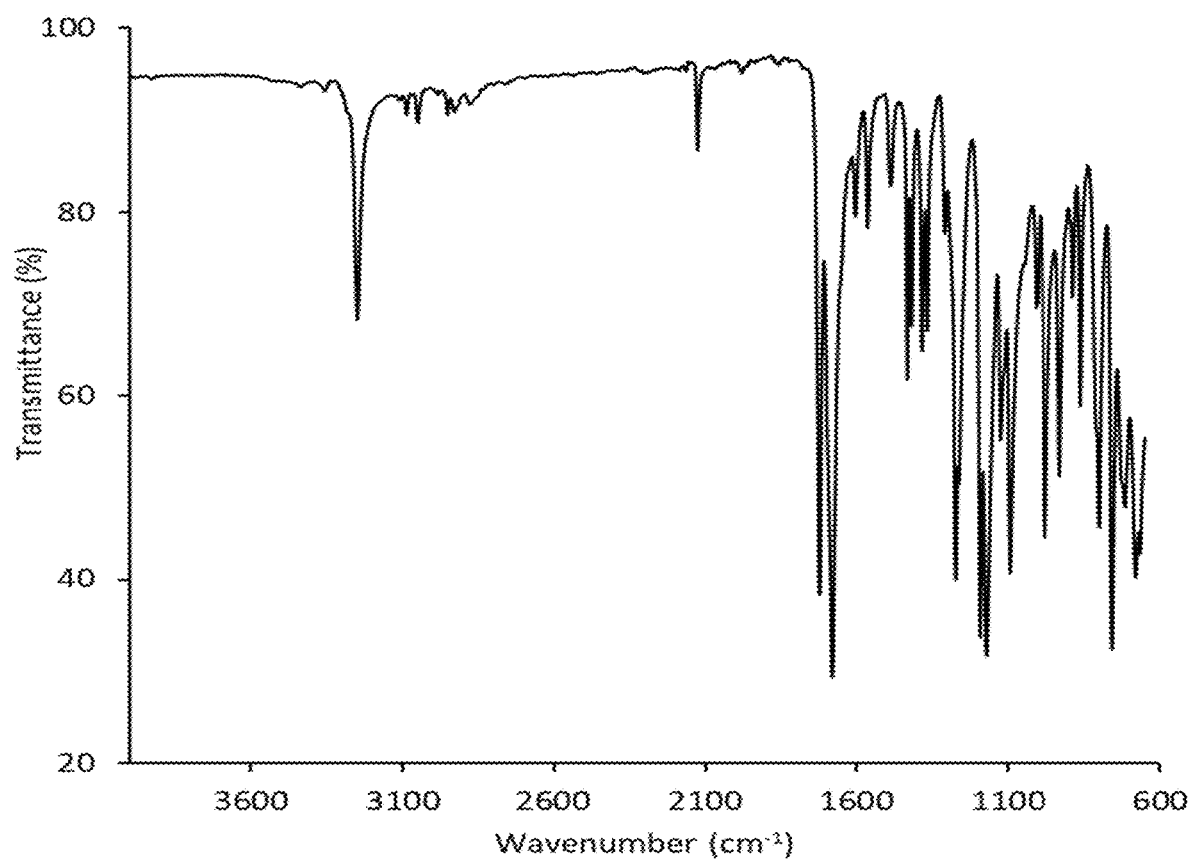
FIG. 2 is an FTIR spectrum of the bifunctional linker of Formula Ib.

A 10 mL round bottom flask was charged with compound 3b (53.5 mg, 0.106 mmol), along with a magnetic stir bar and septa. Acetone (4 mL) and water (0.5 mL) were added and the flask was purged with argon for 15 minutes. Silver nitrate (76.2 mg, 0.449 mmol, 4.2 equiv) was added in one portion, and the reaction mixture was stirred overnight at room temperature. The reaction mixture was diluted with chloroform (100 mL) and passed through a pad of Celite. The organic layer was washed with potassium bromide solution (45 mg in 50 mL of water), dried over anhydrous MgSO4, and concentrated under reduced pressure to provide a yellow solid that was further purified trituration with cyclohexane to yield compound 7 as a white solid (14.6 mg, 0.0675 mmol, 64% yield). FIG. 2 shows the FTIR spectra of compound Ib.

$^1$H NMR (400 MHz, DMSO-$d_6$) δ: 10.56 (s, 1H), 10.52 (s, 1H), 8.51 (s, 1H), 8.39 (d, 1H, J=8.1 Hz), 8.10 (d, 1H, J=8.0 Hz), 5.05 (d, 2H, J=2.3 Hz), 3.70 (t, 1H, J=2.3 Hz). $^{13}$C NMR (100 MHz, $CDCl_3$) δ: 191.7, 191.6, 164.0, 139.5, 136.6, 134.8, 134.2, 133.0, 130.9, 77.03, 75.98, 53.5.

HRMS (EI) found m/z=216.0428 ($M^+$), calculated for $C_{12}H_8O_4$: 216.0423. IR v ($cm^{-1}$): 3249, 2127, 1724, 1682.

Example 2

In this example, a model system is used to illustrate the feasibility of copper-catalyzed azide-alkyne cycloadditions to form triazole polymers.

Ethane-1,2-diyl dipropiolate (4)

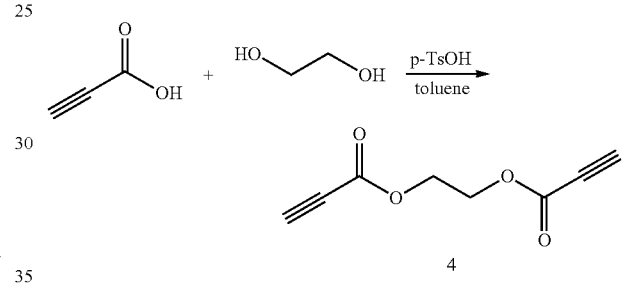

A 250 milliliter (mL) round bottom flask was equipped with magnetic stirring and a Merlic trap. Propiolic acid (10.1 mL, 11.4 g, 162 millimoles (mmol)), toluene (125 mL), ethylene glycol (4.59 mL, 5.11 g, 82 mmol, 0.5 equivalents (equiv)), and para-toluene sulfonic acid monohydrate (1.04 grams (g), 5 mmol, 0.03 equiv) were added to the flask. The reaction mixture was stirred and heated to reflux overnight. The reaction mixture was allowed to cool, and the reaction mixture was diluted with ethyl acetate (100 mL) and hexanes (50 mL) and was washed with water (100 mL, 1×) and saturated sodium bicarbonate (100 mL, 3×). The combined organic layers were washed with brine, dried over anhydrous $MgSO_4$, and concentrated under reduced pressure to provide a brown solid that was further purified by column chromatography ($SiO_2$:EtOAc) to yield 1 as a yellow oil (9.38 g, 56.5 mmol, 70% yield).

$^1$H NMR (400 MHz, $CDCl_3$) δ: 4.93 (s, 4H), 2.95 (s, 2H) matched previous literature reports.[1] $^1$H NMR (400 MHz, DMSO-$d_6$) δ: 4.66 (s, 2H) 4.39 (s, 4H).

IR v ($cm^{-1}$): 3272, 2965, 2119, 1708.

2,2-Bis(azidomethyl)propane-1,3-diol (5)

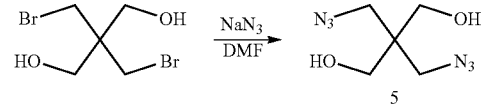

A 250 mL round bottom flask was charged with 2,2-bis(bromomethyl)-1-,3-propanediol (10.05 g, 38.4 mmol), sodium azide (7.94 g, 122 mmol, 3.18 equiv), anhydrous dimethylformamide (80 mL), and a magnetic stir bar. The reaction mixture was stirred and heated to 120° C. overnight. The reaction mixture was allowed to cool, and the mixture was diluted with water (500 mL). An extraction with ethyl acetate (150 mL, 3×) was performed, after which the organic layers were combined and washed with water (100 mL, 5×). The organic phase was washed with saturated ammonium chloride (150 mL, 1×), dried with magnesium sulfate, and further purified with a silica plug (SiO$_2$:EtOAc) before drying under rotary evaporation to yield 2 as a yellow oil (5.38 g, 28.9 mmol, 75% yield).

$^1$H NMR (400 MHz, CDCl$_3$) 3.64 (s, 4H), 3.43 (s, 4H), 2.03 (s, 2H) was similar to previous literature reports. $^1$H NMR (400 MHz, D$_2$O) 3.50 (s, 4H), 3.40 (s, 4H). $^1$H NMR (400 MHz, DMSO-d$_6$) 4.76 (t, 2H, J=4.96 Hz), 3.29 (s, 4H), 3.27 (d, 4H, J=4.96 Hz).

IR ν (cm$^{-1}$): 3346, 2935, 2887, 2092.

Polymer 6.

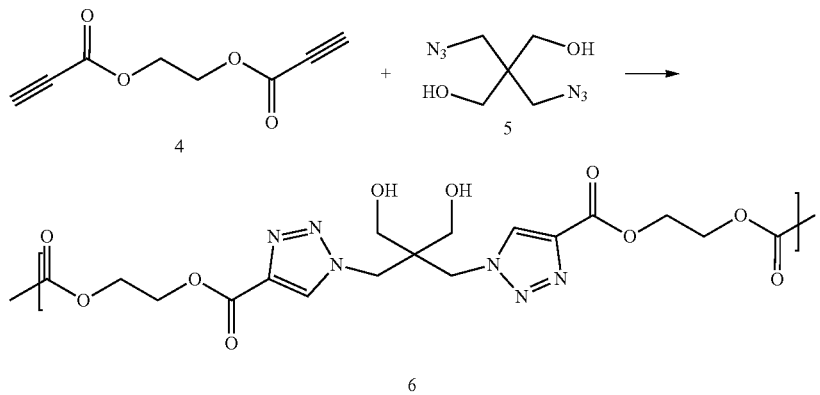

Figure 3:
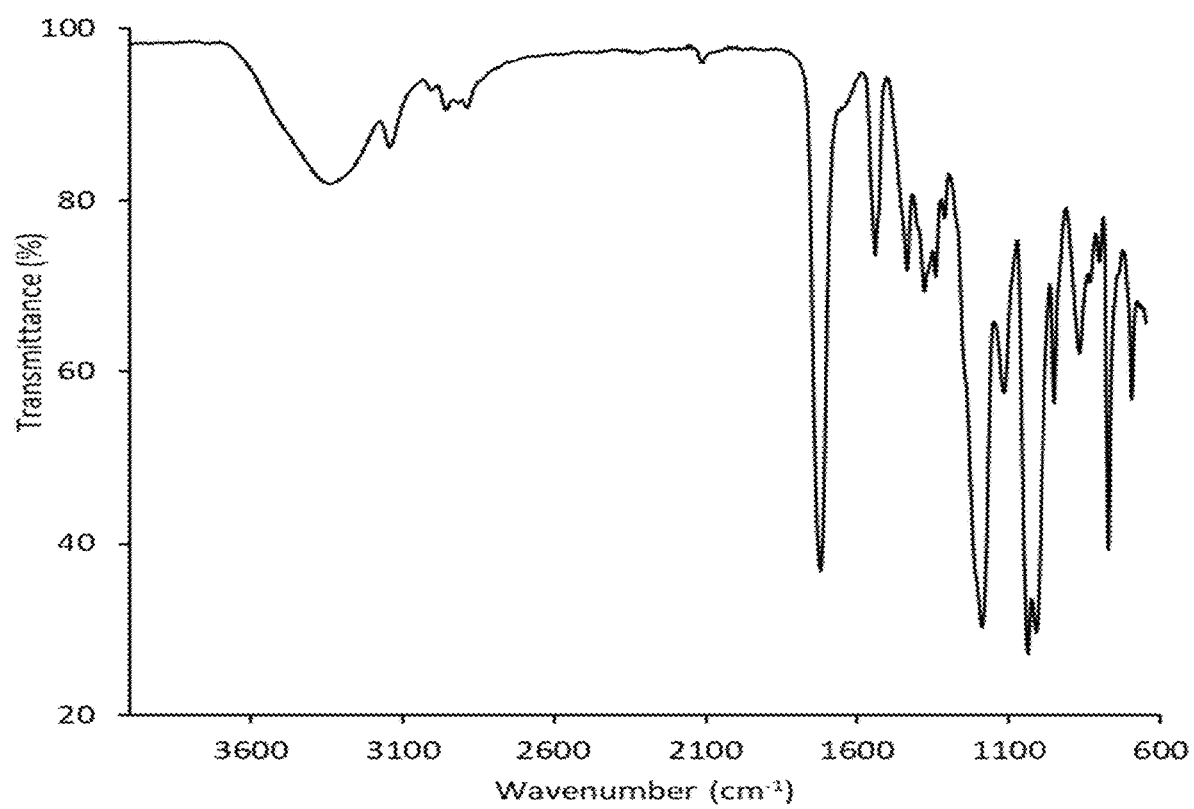
FIG. 3 is a Fourier transform infrared (FTIR) spectrum of neat polymer 6 made neat.

A vial open to ambient conditions was charged with compound 4 (50 mg, 0.30 mmol) and 5 (56 mg, 0.30 mmol), vortexed briefly, and allowed to react overnight at room temperature. An FTIR of neat polymer 6 is shown in FIG. 3.

$^1$H NMR (400 MHz, DMSO-d$_6$) δ: 8.67 (br, 2H), 5.09 (br, 2H), 4.93 (br, 2H), 4.61 (br, 4H), 4.50 (br, 4H), 3.24 (br, 2H), 3.16 (br, 4H).

Figure 4:
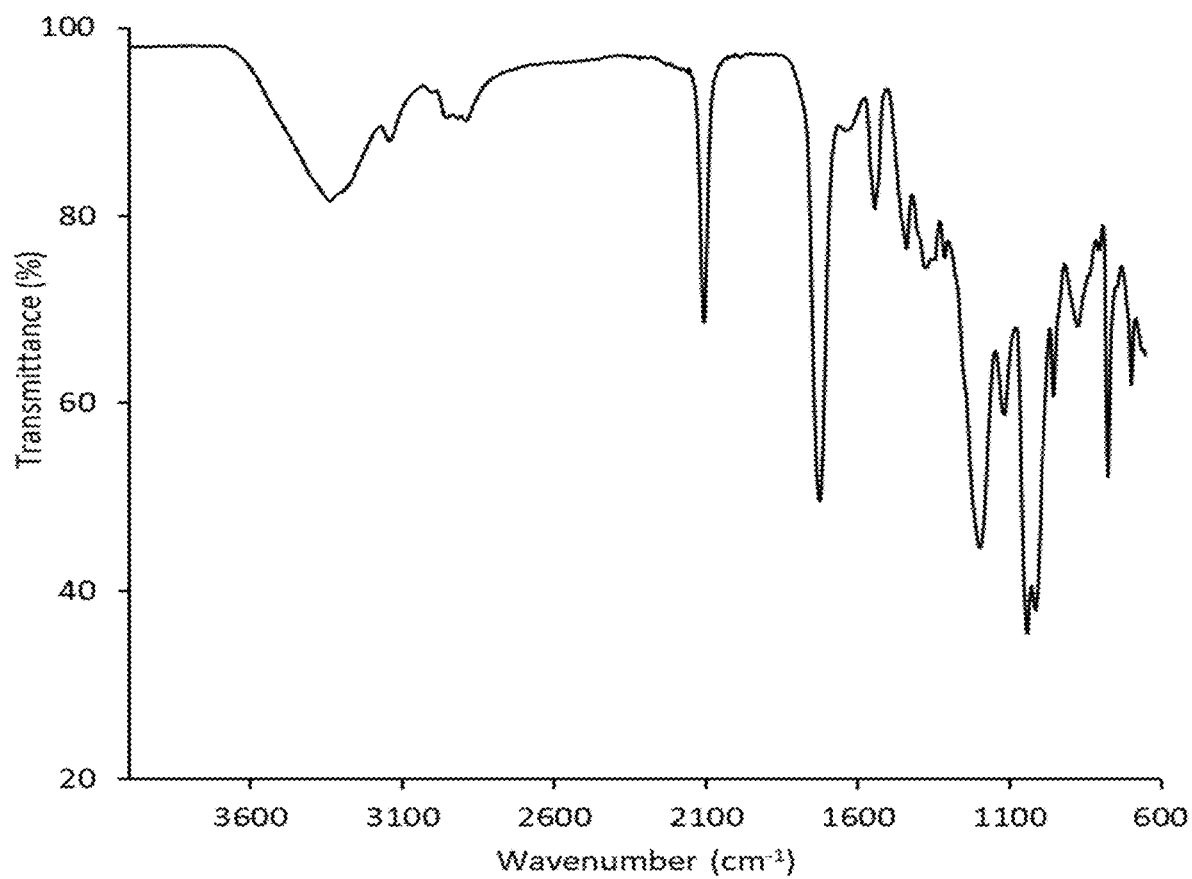
FIG. 4 is an FTIR spectrum of polymer 6 made in 1:1 water:DMSO by volume.
Figure 5:
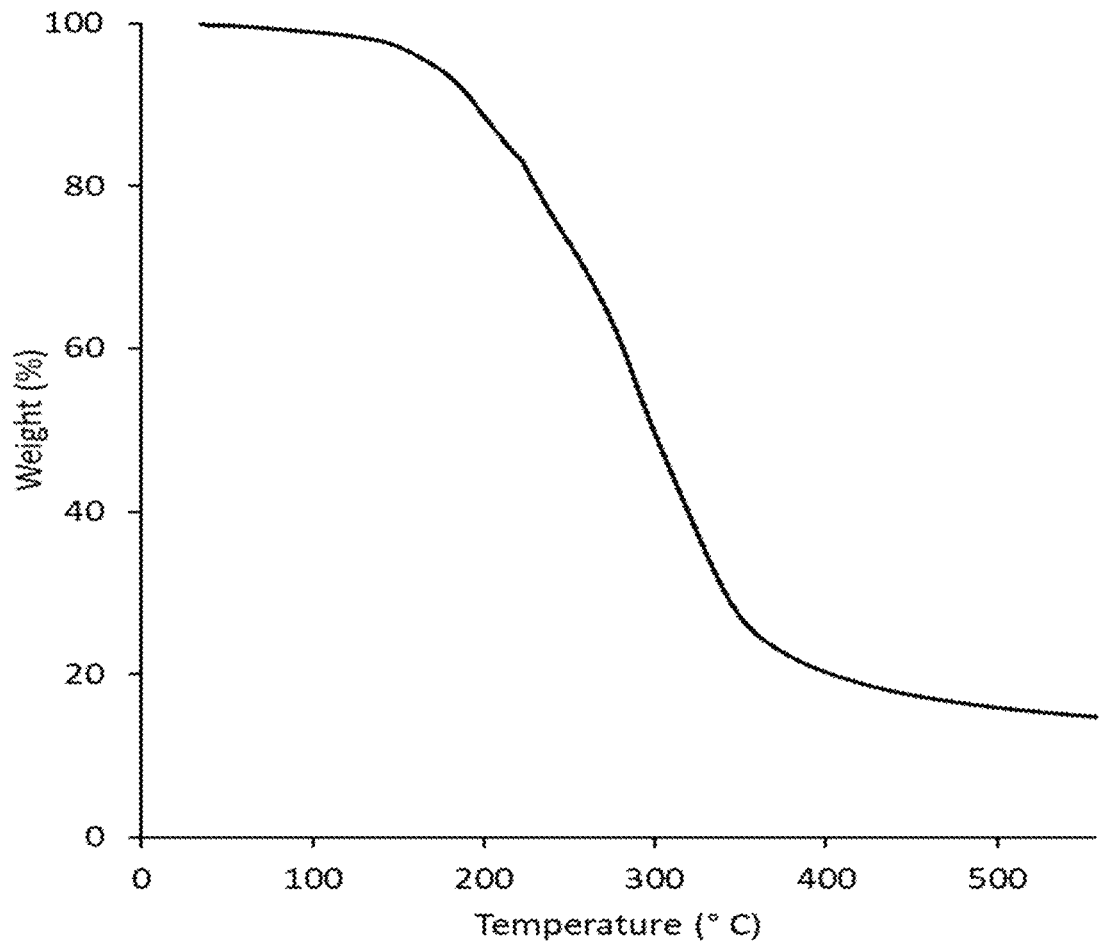
FIG. 5 is a thermogravimetric analysis thermogram of polymer 6 made in 1:1 water:DMSO by volume.

An FTIR of polymer 6 polymerized in a mixture of 1:1 water:DMSO by volume is shown in FIG. 2. FIG. 4 shows a TGA thermogram of polymer 6 polymerized in a mixture of 1:1 water:DMSO by volume.

Example 3

In this example, a protected lysine is reacted with the dialdehyde moiety of the bifunctional linker of Formula Ib to form a lysine conjugate including an isoindole group. In the lysine-Ib conjugate acetate salt, two regioisomers are formed, 7a and 7b.

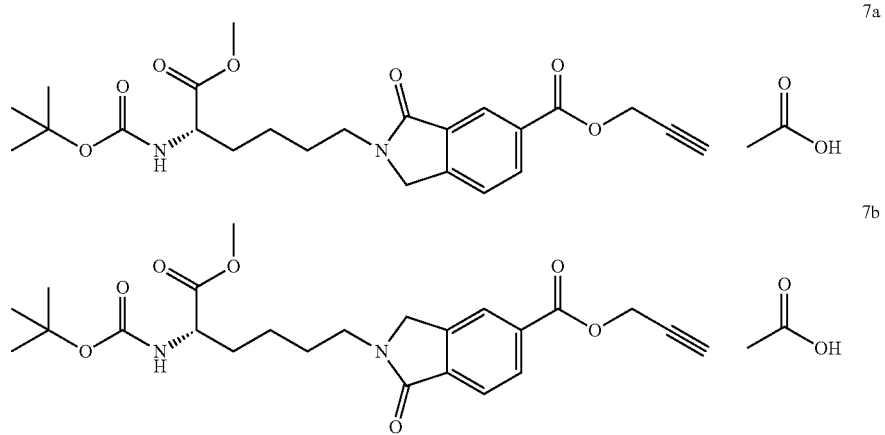

Figure 6:
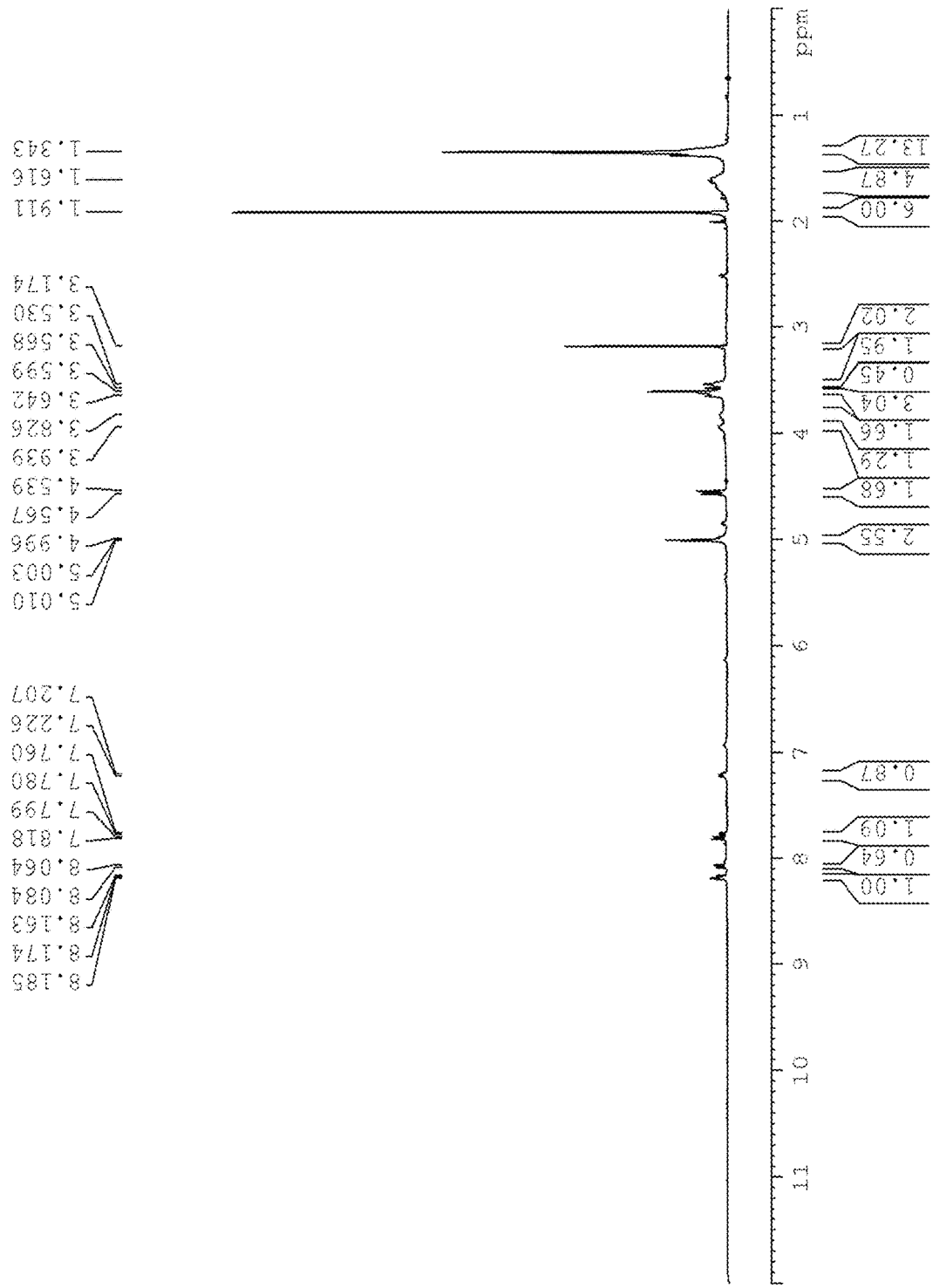
FIG. 6 shows a $^1$H NMR spectrum of a lysine-bifunctional linker Ib conjugate showing both regioisomers of Formulas 7a and 7b.

To form the salts, an NMR tube was charged with Boc-L-lysine methyl ester acetate salt (32.6 mg, 0.102 mmol) in DMSO-$d_6$ and a $^1$H NMR spectrum was taken. To the solution bifunctional linker Ib (21.4 mg, 0.100 mmol) was added, and the solution was vortexed for 1 min. A $^1$H NMR spectrum was then obtained, as shown in FIG. 6.

LRMS (ESI) found m/z=459.0 (M$^+$), calculated for $C_{24}H_{30}N_2O_7$: 458.2. LRMS (ESI) found m/z=481.0 (M$^+$+Na), calculated for $C_{24}H_{30}N_2O_7$Na: 481.2.

Example 4

In this example, the bifunctional linker of Formula Ib is conjugated to a protein. Conjugation to the same protein with N-propargylmaleimide, a known cysteine linker, is also performed as a control.
Red Fluorescent Protein (RFP) Expression and Purification.

RFP was expressed from the pBAD-DsRED plasmid (addgene) in *E. coli* BL21(DE3). 1 L cultures were grown at 37° C. with shaking to an optical density (OD) of 0.5 and induced with arabinose at a final concentration of 1%. At induction, the temperature was shifted to 18° C. and cultures were grown overnight. Pellets from the overnight culture were harvested by centrifugation and stored at −80° C. until use. Cells were thawed and resuspended in 100 mL of 500 mM, Tris 8.0 buffer (NaCl 50 mM). The homogenous cell mixture was sonicated for 15 minutes at 80 amps and centrifuged at 15,000×G for 2 hours to remove supernatant. The supernatant was then purified using a His GraviTrap TALON cobalt column (GE Healthcare, 29-0005-94). For column purification, 500 mM NaCl, 50 mM Tris 8.0 buffer, 500 mM NaCl, 50 mM Tris 8.0, 20 mM Imidazole buffer, and 500 mM NaCl, 50 mM Tris 8.0, 500 mM Imidazole buffer were used for the equilibrium, wash, and elution buffers, respectively. The eluted protein was dialyzed overnight in 2 L of 250 mM NaCl, 50 mM Tris 8.0, 10% Glycerol buffer using SNAKESKIN™ Dialysis Tubing, 10K MWCO, 35 mm (ThermoFisher Scientific, 88245). The purified RFP was flash frozen with liquid nitrogen and store in −80° C. Purity was confirmed by SDS-PAGE.
RFP-Bifunctional Linker Ib Conjugate.

Flash-frozen, purified RFP was diluted to 0.1 mg/mL in phosphate-buffered saline. Compound Ib was solubilized in 100% methanol at 100 μg/mL. The solution of Compound Ib was in a 10:1 ratio or 1:1 of RFP to conjugate Ib was added to the diluted RFP and allowed to react for 1 hour at room temperature. The reaction product was concentrated down using a 10 kDa spin concentrator (Millipore Sigma, CLS431478) to 1 mg/mL for application, providing an RFP-bifunctional linker Ib conjugate of Formula IIIb.
RFP-N-Propargylmaleimide Conjugate Flash-frozen, purified RFP was diluted to 0.1 mg/mL in phosphate-buffered saline. N-propargylmaleimide was solubilized in 100% methanol at 50 μg/mL. A 10:1 ratio of maleimide to RFP was added to diluted RFP and allowed to react for 16 hours at room temperature. The reaction product was concentrated to 1 mg/mL using a 10 kDa spin concentrator (Millipore Sigma, CLS431478) for application.
Analysis and Results Mass peptide fingerprint analysis was utilized to assess the bioconjugation of maleimide and the bifunctional linker of Formula Ib with RFP. RFP without linker was used as a control, and trypsin digestion followed by MS/MS analysis displayed 99% Mascot coverage with 435 total matches as shown in Table 1. The cysteine linker, N-propargylmaleimide (MAL), was added to RFP in a 10:1 (N-propargylmaleimide:RFP) ratio to form RFP-mal and the same evaluation revealed 100% coverage with 498 total matches (Table 1). Linker Ib was allowed to react with RFP at a ratio of 10:1 (Ib:RFP) and the evaluation displayed 61% coverage and only 46 matches (Table 1). Trypsin digestion cleaves proteins at the arginine and lysine residues, and it is hypothesized that the large excess of linker Ib interfered with the digestion step. Thus, linker Ib was allowed to react with RFP to form RFP-Ib at a ratio of 1:1 (Ib:RFP) and the evaluation showed a 99% coverage with 456 total matches as shown in Table 1.

TABLE 1

Summary of mass peptide fingerprinting results

| | Coverage | Total matches | Sequences | Sequences with modification |
|---|---|---|---|---|
| 1:1 RFP:Ib | 99% | 456 | 40 | 19 |
| 1:10 RFP:Ib | 61% | 46 | 15 | 5 |
| 1:10 RFP:MAL | 100% | 498 | 77 | 2 |
| No linker | 99% | 435 | 42 | — |

Figure 7:
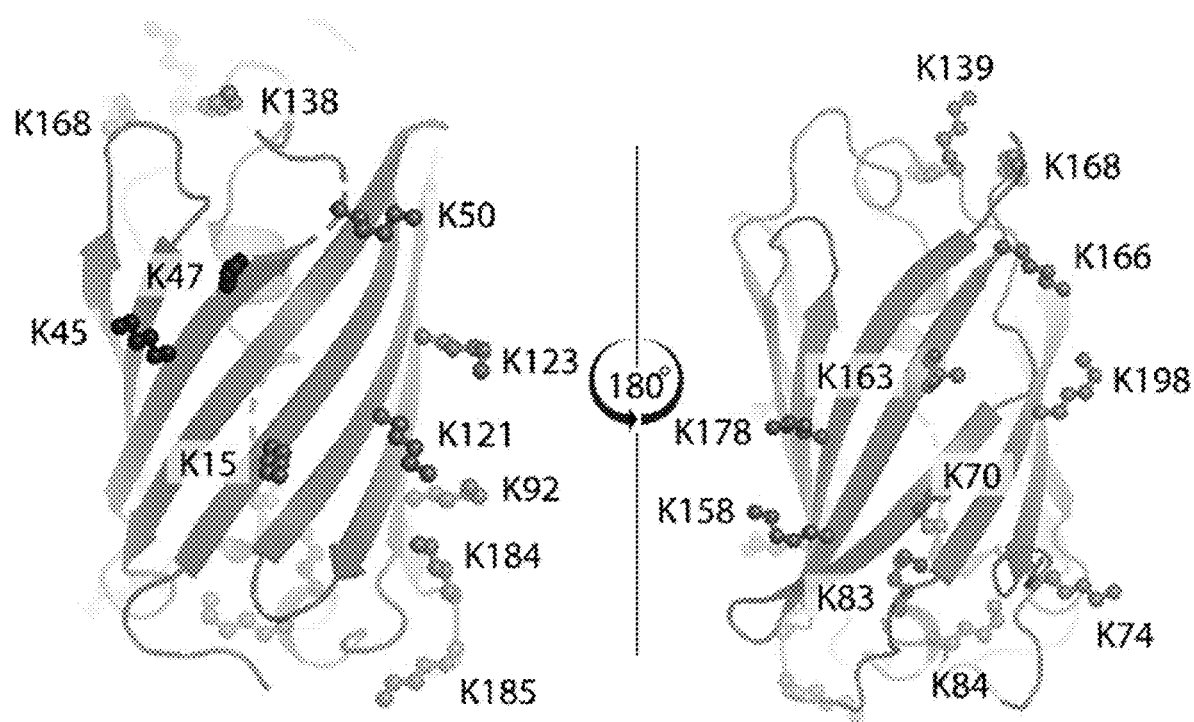
FIG. 7 is a schematic structure of red fluorescent protein (RFP) showing lysine residues as sticks and balls (PDB 1GGX), where residues that unambiguously react with ortho-dipthalaldehyde (oPA) moiety are shown in green (Mascot site analysis probability >89%), residues that may react with the oPA moiety are shown in blue (peptide fragment contained at least 2 lysine residues with similar site analysis probabilities), and residues that do not react with lysine are shown in red (no labeling detected by mass spectrometry)

Mass spectrometry data from the 1:1 reaction was further analyzed to identify which residues were modified. Of the 21 lysines, 12 were unambiguously modified and modification could not be detected for five positions (FIG. 7 and Table 2). FIG. 7 shows a schematic structure of red fluorescent protein (RFP) showing lysine residues as sticks and balls (PDB 1GGX), where residues that unambiguously react with the bifunctional Ib are shown in green (Mascot site analysis probability >89%), residues that may react with bifunctional Ib are shown in blue (peptide fragment contained at least 2 lysine residues with similar site analysis probabilities), and residues that do not react with lysine are shown in red (no labeling detected by mass spectrometry). The remaining lysines were detected in peptide fragments with modification, but the exact position of modification was confounded by the presence of multiple lysines with similar site probabilities. No arginine modifications were detected.

TABLE 2

Summary of site analysis used to identify lysines reactive to linker Ib in 1:1 sample*

| Lysine position | Site analysis probability | Interfering positions |
|---|---|---|
| 15 | Not covered | |
| 45 | 49.95 | 47 |
| 47 | 49.95 | 45 |
| 50 | Not detected | |
| 70 | Not detected | |
| 74 | 100 | |
| 83 | 50 | 84 |
| 84 | 100 | |
| 92 | 99.99 | |
| 121 | Not detected | |
| 123 | 99.96 | |
| 138 | 89.16 | |
| 139 | 100 | |
| 158 | 99.22 | |
| 163 | 48.04 | 158 |
| 166 | 99.95 | |
| 168 | 100 | |
| 178 | 100 | |
| 184 | Not detected | |
| 185 | 99.83 | |
| 198 | 100 | |

*Middle column shows the highest score from across all sequences. Right column shows positions causing ambiguities (i.e., appears in the same peptide fragment and not differentiated by fragmentation pattern)

Example 5

In this example, unconjugated RFP and the two RFP-linker conjugates of Example 4 are applied to a substrate surface using a copper-containing paint as a catalyst, and to an untreated glass and an untreated aluminum substrate.
Preparation of Copper-Painted Substrates.

Stainless steel disks (Wagner) were sand blasted and primed with three coats of MIL-DTL-24441, Type III A/B (Sherwin-Williams) diluted with Polane Reducer K69 (Sherwin-Williams). SEAGUARD® Ablative Antifouling coating (Sherwin-Williams, Red) was applied to the primed surface in five coats and allowed to dry overnight.
General Procedure for Substrate Binding.

Sodium ascorbate (5 mg, 0.03 mmol) was dissolved in RFP/buffer solution (100 µL, 1 mg/mL protein content, containing native RFP, RFP-MAL conjugate, or RFP-Ib conjugate). DMSO (100 µL) was added dropwise to the solution to limit local heating. The dipropiolate 4 (25 mg, 0.15 mmol) and the diazide 5 (28 mg, 0.15 mmol) prepared as above were also added to the solution. The entire mixture was vortexed briefly and applied to a copper painted substrate with a paintbrush. The substrate was then washed vigorously in a beaker of water to remove any unbound RFP or polymer 6. Three repetitions for of each of RFP, RFP-MAL conjugate, or RFP-Ib conjugate were performed.

A challenge to the analysis of any binding by fluorescence microscopy is that RFP reversibly binds copper(II), which quenches the fluorescence of the protein. Ideally, there would not be sufficient time during the experiment for copper to leach into solution, oxidize to copper(II), and inhibit fluorescence. In an attempt to limit any possible quenching, the short reaction time of 5 minutes was chosen. This resonant time constraint after application limits the amount of adhesive polymerization that can occur; as chains of a certain length are required to tether the protein to the surface, rapid polymerization was of the utmost importance.

The same procedure was used to coat unpainted glass and unpainted aluminum with RFP-Ib conjugate, but required longer reaction times (30 minutes) due to the lack of a copper catalyst in those surfaces. However, because those surfaces were not treated with the copper paint, the longer reaction times did not come with the risk of fluorescent quenching due to copper binding. The glass and aluminum substrates were not washed after reaction.
Analysis and Results A set fluorescent microscopy images were made to assess the amount of RFP that remained bound to the surface after washing. The images were analyzed by ImageJ software with threshold range 40-250. To quantify the RFP, the Analyze Particles plugin was used with size: 10-infinite and no restrictions on circularity. Results are shown in Table 3.

TABLE 3

RFP retention percentage on copper-painted stainless steel

|  | Count (Pre) | Average (Pre) | Count (Post) | Average (Post) | Retained (%) |
| --- | --- | --- | --- | --- | --- |
| RFP | 141 | 93 | 3 | 2 | 2 |
|  | 67 |  | 1 |  |  |
|  | 71 |  | 1 |  |  |
| RFP-MAL | 130 | 94 | 16 | 13 | 13 |
|  | 43 |  | 11 |  |  |
|  | 109 |  | 11 |  |  |
| RFP-Ib | 262 | 209 | 57 | 58 | 28 |
|  | 145 |  | 77 |  |  |
|  | 221 |  | 39 |  |  |

Figure 8:
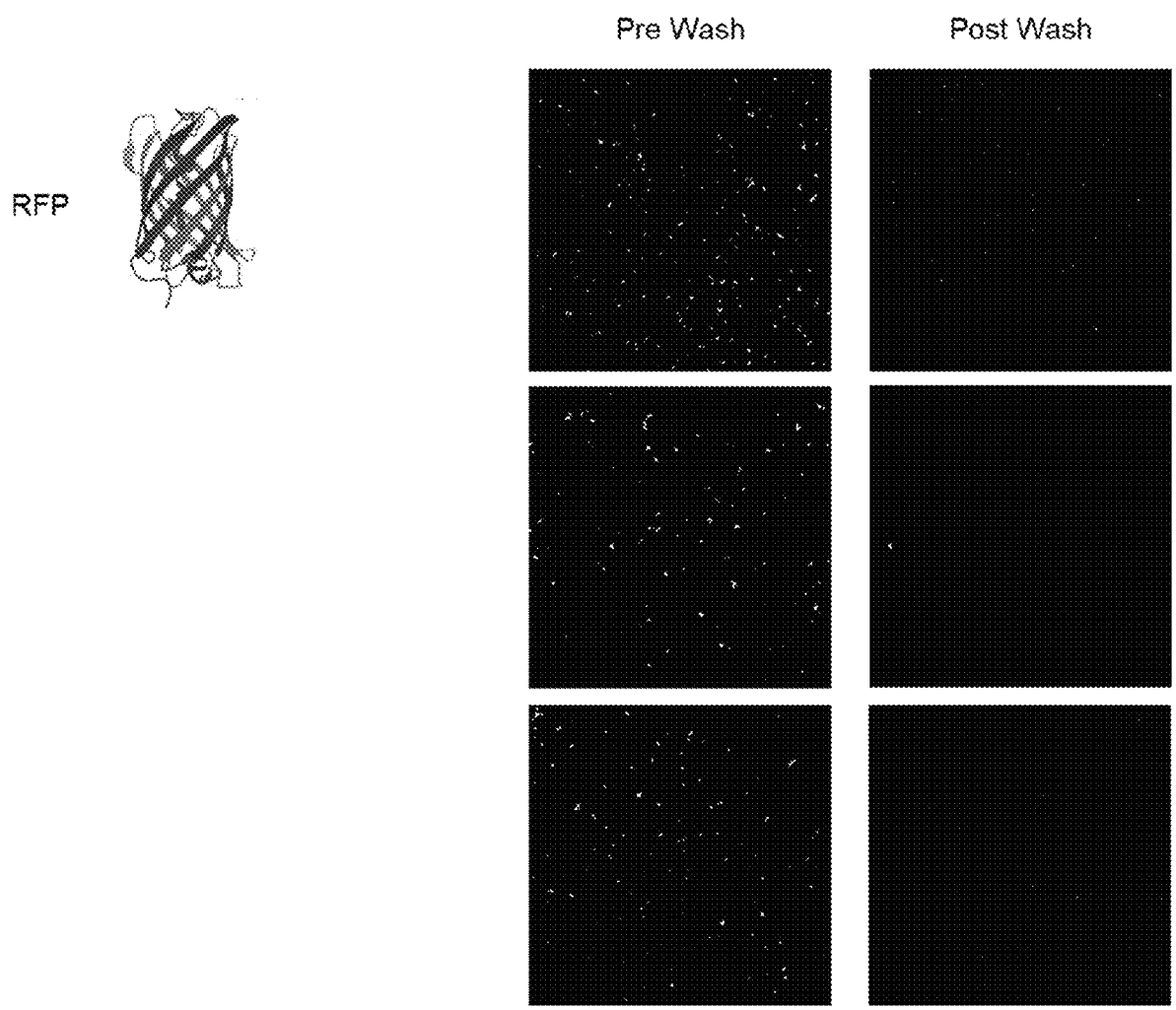
FIG. 8 show representative fluorescent microscope images taken before (Pre Wash) and after (Post Wash) washing of a copper-painted disk treated with RFP with no linker.
Figure 9:
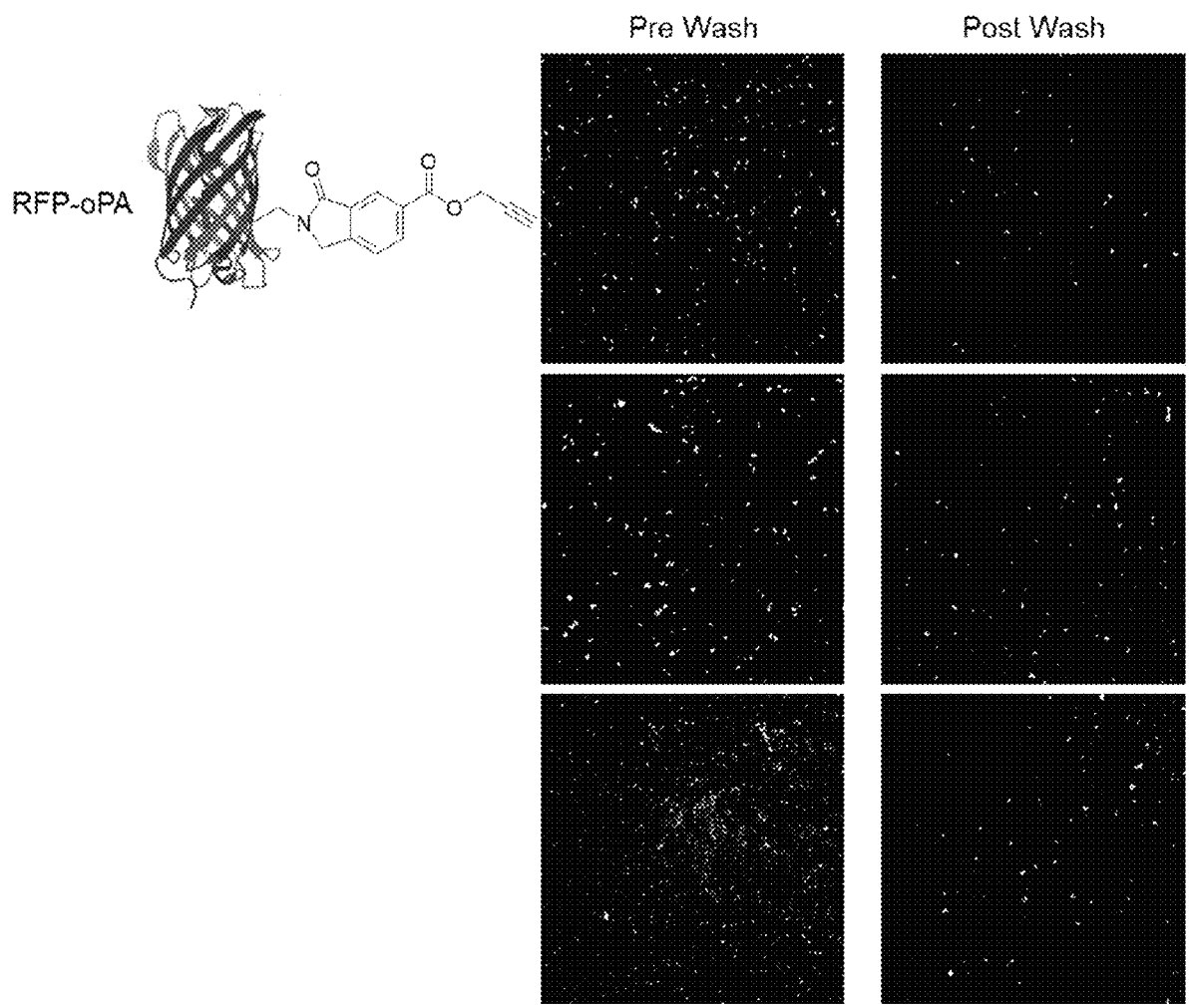
FIG. 9 shows representative fluorescent microscope images taken before (Pre Wash) and after (Post Wash) washing of a copper-painted disk treated with an RFP-malemide conjugate.
Figure 10:
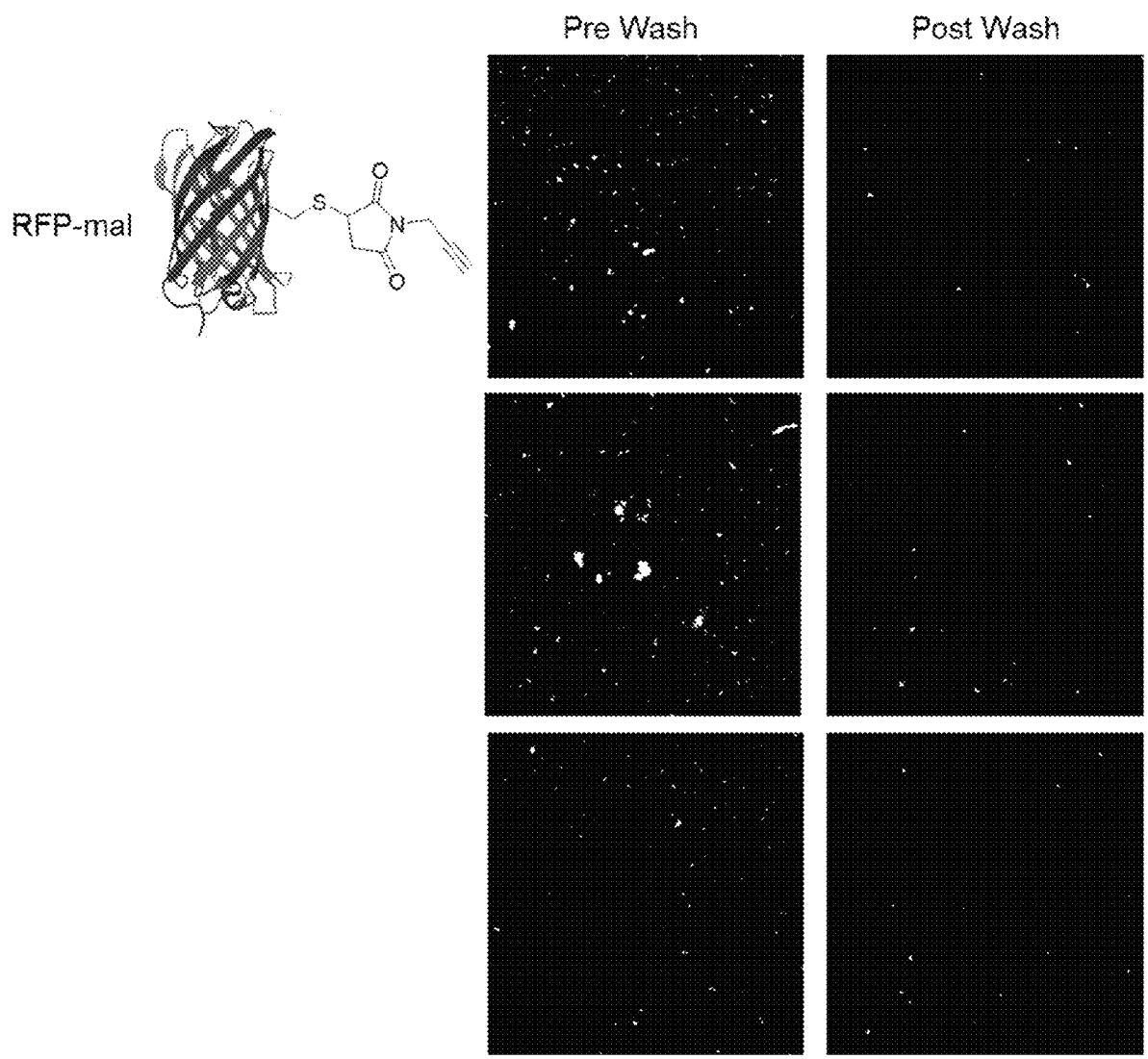
FIG. 10 shows representative fluorescent microscope images taken before (Pre Wash) and after (Post Wash) washing of a copper-painted disk treated with an RFP-Compound MB conjugate.

As can be seen from Table 3 and the images, the control set, without any linker, showed RFP on the sample before washing (FIG. 6, pre-wash) but only 2% of the RFP was retained after washing (FIG. 6, post wash). The RFP-MA conjugate displayed a similar amount of fluorescence in the pre-wash stage (FIG. 6, pre-wash) but retained a larger amount of RFP signal (13%) post-wash (FIG. 7, post wash) than the control set. The bisconjugate of Formula VIIb (RFP-Formula IIIb conjugate) displayed the largest retention of fluorescence, with 28% remaining after the washing step (FIG. 8, post wash). While not wishing to be bound by this theory, it is believed that the increased binding efficiency using the bifunctional linker Ib compared to the maleimide linker is a result of multiple lysine residues being available for bioconjugation. This allows the RFP to act essentially as a crosslinker between multiple triazole polymer residues, whereas there is only one cysteine residue, such that any RFP-mal conjugate acts essentially as a chain terminator.

Figure 11:
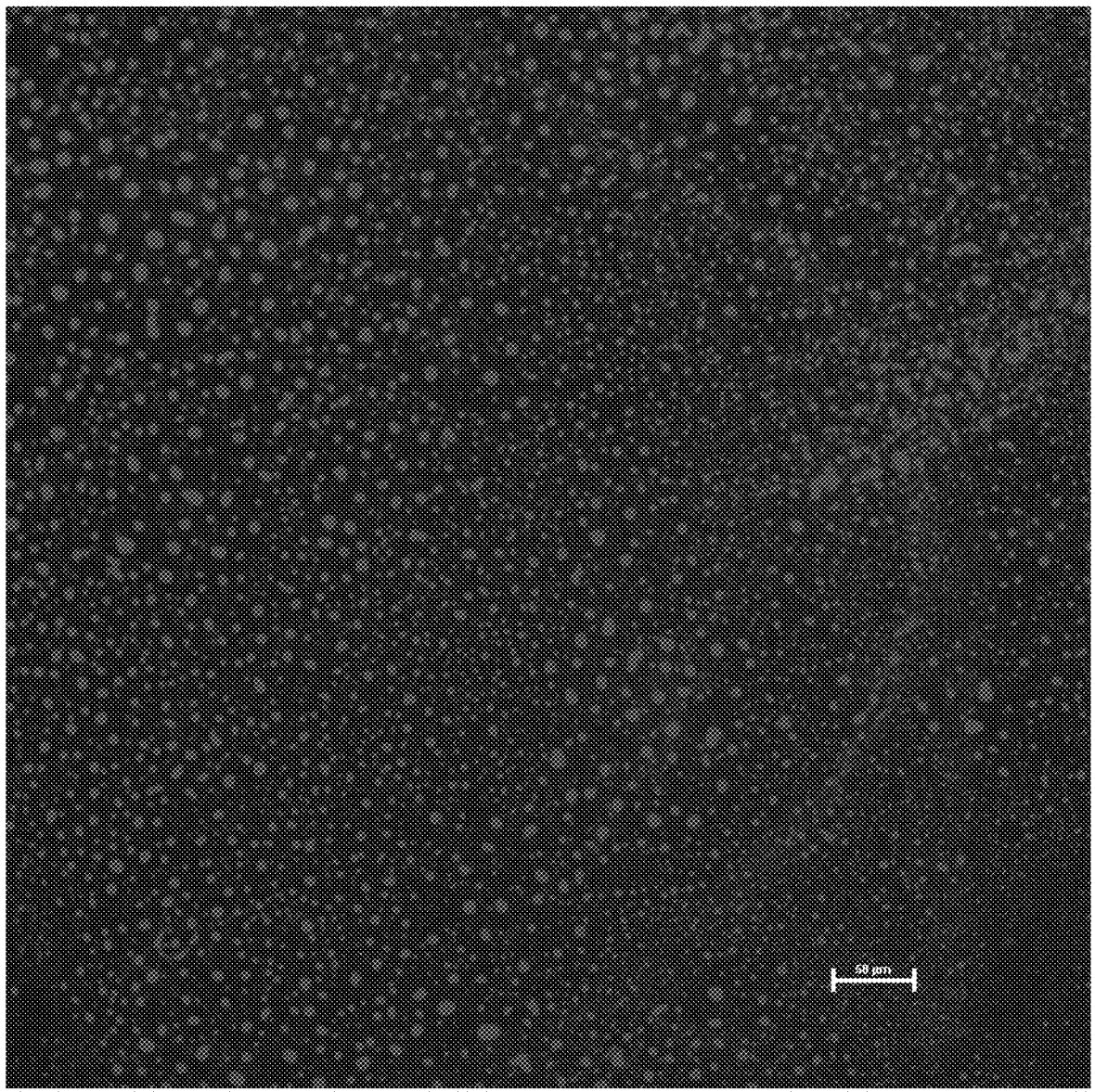
FIG. 11 is a photograph that shows an RFP-oPA/SA/1/2 mixture applied to glass and allowed to sit for 30 minutes, where the scale bar shows 50 micrometers.
Figure 12:
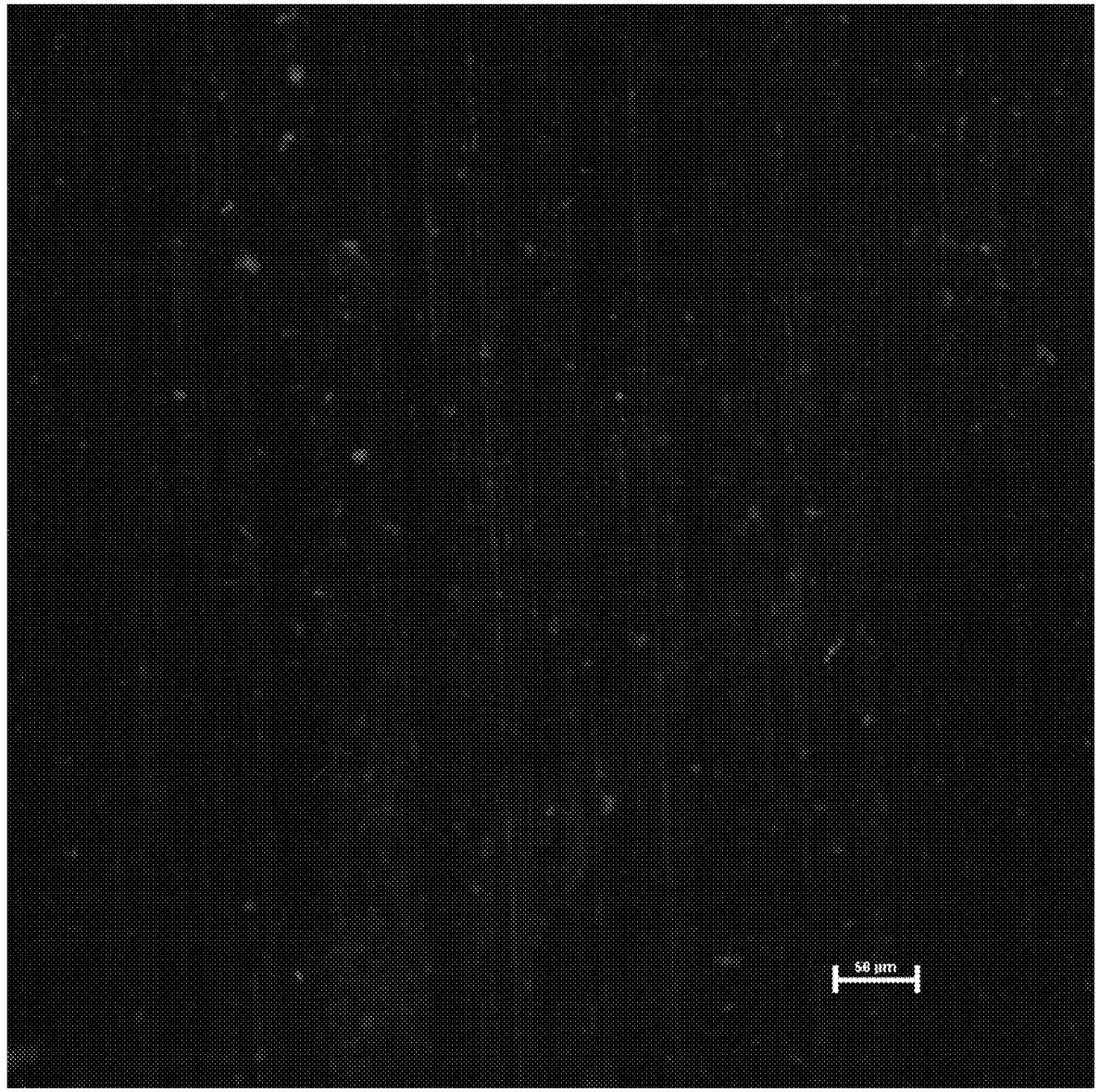
FIG. 12 is a photograph that shows an RFP-oPA/SA/1/2 mixture applied to aluminum and allowed let to sit for 30 min, where the scale bar shows 50 micrometers.

Finally, an image of the RFP-Ib coated plain glass and plain aluminum substrates is shown in FIG. 11 and FIG. 12, respectively. These images show that the RFP-adhesive polymer adhered well to each of the surfaces, suggesting that the polymer can adhere to a variety of different types of surfaces.

Terminology

The terms "a" and "an" do not denote a limitation of quantity, but rather denote the presence of at least one of the referenced items. The term "or" means "and/or" unless clearly indicated otherwise by context. The terms "comprising," "having," "including," and "containing" are to be construed as open-ended terms (i.e., meaning "including, but not limited to"). The opened ended term "comprising" includes the intermediate and closed terms "consisting essentially of" and "consisting of." Thus, the compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended for illustration and does not pose a limitation on the scope of the disclosure unless otherwise claimed. No language in the specification should be construed as indicating any non-claimed element as essential to the practice of the invention. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

When an element such as a layer, film, region, or substrate is referred to as being "on" another element, it can be directly on the other element or intervening elements may also be present. In contrast, when an element is referred to as being "directly on" another element, there are no intervening elements present.

Compounds are described using standard nomenclature. Unless defined otherwise, all technical and scientific terms used herein have the same meaning as is commonly understood by one of skill in the art to which this invention belongs.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

The term "substituted" means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("—") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other aspects include alkyl groups having from 1 to 8 carbon atoms, 1 to 4 carbon atoms or 1 or 2 carbon atoms, e.g., $C_1$-$C_8$alkyl, $C_1$-$C_4$alkyl, and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more carbon-carbon double bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more double carbon-carbon triple bonds that may occur at any stable point along the chain, having the specified number of carbon atoms.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Cycloalkyl" is a saturated hydrocarbon ring group, having the specified number of carbon atoms, usually from 3 to about 7 carbon atoms. Examples of cycloalkyl groups include cyclopropyl, cyclobutyl, cyclopentyl, or cyclohexyl as well as bridged or caged saturated ring groups such as norbornane or adamantane. "—($C_0$-$C_n$alkyl)cycloalkyl" is a cycloalkyl group attached to the position it substitutes either by a single covalent bond ($C_0$) or by an alkylene linker having 1 to n carbon atoms.

"Halo" or "halogen" means fluoro, chloro, bromo, or iodo.

"Heteroaryl" is a stable monocyclic aromatic ring having the indicated number of ring atoms which contains from 1 to 3, or in some aspects from 1 to 2, heteroatoms chosen from N, O, and S, with remaining ring atoms being carbon, or a stable bicyclic or tricyclic system containing at least one 5- to 7-membered aromatic ring which contains from 1 to 3, or in some aspects from 1 to 2, heteroatoms chosen from N, O, and S, with remaining ring atoms being carbon. Monocyclic heteroaryl groups can have from 5 to 7 ring atoms. In some aspects bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Heteroaryl groups include, but are not limited to, oxazolyl, piperazinyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, isothiazolyl, and isoxazolyl.

"Heterocycle" is a saturated, unsaturated, or aromatic cyclic group having the indicated number of ring atoms containing from 1 to about 3 heteroatoms chosen from N, O, and S, with remaining ring atoms being carbon. Examples of heterocycle groups include piperazine and thiazole groups.

"Heterocycloalkyl" is a saturated cyclic group having the indicated number of ring atoms containing from 1 to about 3 heteroatoms chosen from N, O, and S, with remaining ring atoms being carbon. Examples of heterocycloalkyl groups include tetrahydrofuranyl and pyrrolidinyl groups.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

A "biomolecule" means any compound or polymer, natural, synthetic, or semi-synthetic, found in natural systems or of use in natural systems.

A "protein" means sequence of peptides having a length of 6 or more, 20 or more, or 50 or more, or 100 or more peptides. The peptides can be natural, synthetic, or semi synthetic. The protein can be natural, synthetic, or semi synthetic, and can be modified from its natural state.

A "patient" means a human or non-human animal in need of medical treatment. Medical treatment can include treatment of an existing condition, such as a disease or disorder, preventative treatment, or diagnostic treatment. In some aspects the patient is a human patient.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A compound of Formula I

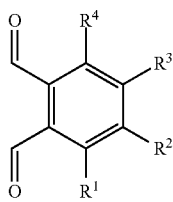

(Formula I)

wherein in Formula I,

R$^1$ to R$^4$ are each independently hydrogen, halogen, cyano, nitro, C$_1$-C$_6$alkyl, C$_0$-C$_6$alkyl(C$_3$-C$_7$cycloalkyl), —C$_0$-C$_6$alkyl(heterocycloalkyl), —C$_0$-C$_6$alkyl(aryl), or —C$_0$-C$_6$alkyl(heteroaryl), wherein groups except hydrogen, halogen, cyano, and nitro are optionally substituted with halogen, cyano, nitro, a C$_1$-C$_6$alkyl, a C$_3$-C$_7$cycloalkyl, a heterocycloalkyl, a heteroaryl, or an aryl, and at least one of R$^1$ to R$^4$ is —COOR$^5$; and R$^5$ is —C$_0$-C$_{10}$alkyl(C$_2$-C$_{10}$alkynyl) or —C$_0$-C$_{10}$alkyl-C$_2$-C$_{10}$alkenyl(C$_2$-C$_{10}$alkynyl).

2. The compound of claim 1, wherein

R$^1$, R$^2$, and R$^4$ is each independently hydrogen or C$_1$-C$_6$alkyl optionally substituted with halogen, cyano, nitro, C$_3$-C$_7$cycloalkyl, or C$_6$-C$_{12}$ aryl;

R$^3$ is —COOR$^5$; and

R$^5$ is —C$_1$-C$_6$alkyl(C$_2$alkynyl).

3. The compound of claim 1, where the compound is of Formula Ib

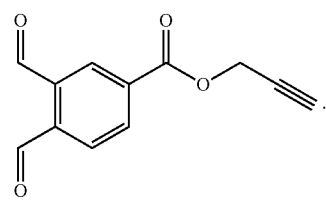

(Formula Ib)

4. A process of synthesizing the compound of claim 1, the process comprising:

reacting a dimethylarylcarboxylic acid of Formula 1

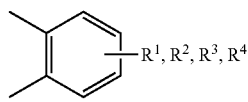

(Formula 1)

wherein R$^1$, R$^2$, R$^3$, and R$^4$ are as defined in Formula I except that at least one of R$^1$, R$^2$, R$^3$, and R$^4$ is —COOH, with a halogenating agent to provide a tetrahalomethylarylcarboxylic acid of Formula 2;

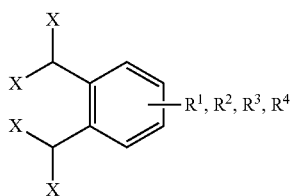

(Formula 2)

wherein R$^1$, R$^2$, R$^3$, and R$^4$ are as defined in Formula I, except that at least one of R$^1$, R$^2$, R$^3$, and R$^4$ is —COOH, and X is a halide;

reacting the tetrahalomethylarylcarboxylic acid of Formula 2 with an alkyne compound having a leaving group to afford a carboxylate ester of Formula 3

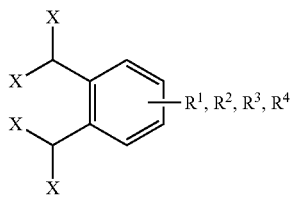

(Formula 3)

wherein R$^1$, R$^2$, R$^3$, R$^4$, and R$^5$ are as defined in Formula I, and X is a halide; and oxidizing the carboxylate ester of Formula 3 using an oxidizing agent to afford the compound of Formula I.

5. The process of claim 4, wherein the oxidizing agent is silver nitrate.

* * * * *